US006780628B2

(12) United States Patent
Anderson et al.

(10) Patent No.: US 6,780,628 B2
(45) Date of Patent: Aug. 24, 2004

(54) ENZYME TREATMENT

(75) Inventors: David M. Anderson, Rockville, MD (US); Lin Liu, Rockville, MD (US); Humg-Yu Hsiao, Rockville, MD (US); Douglas W. Fodge, Derwood, MD (US)

(73) Assignee: Chemgen Corporation, Gaithersburg, MD (US)

( * ) Notice: Subject to any disclaimer, the term of this patent is extended or adjusted under 35 U.S.C. 154(b) by 58 days.

(21) Appl. No.: 09/731,971

(22) Filed: Dec. 8, 2000

(65) Prior Publication Data

US 2002/0048576 A1 Apr. 25, 2002

Related U.S. Application Data

(60) Provisional application No. 60/169,935, filed on Dec. 10, 1999.

(51) Int. Cl.$^7$ .............................. A23L 1/31; C12N 9/00; C12N 9/20; C12N 9/14
(52) U.S. Cl. .............................. 435/198; 435/4; 435/6; 435/183; 435/195; 426/2; 426/56; 426/531
(58) Field of Search ............................ 435/4, 6, 69.1, 435/183, 195, 198, 252.3, 320.1, 252.31, 272, 267; 426/2, 56, 531; 536/23.2

(56) References Cited

U.S. PATENT DOCUMENTS

| | | | |
|---|---|---|---|
| 4,079,125 A | 3/1978 | Sipos | 424/32 |
| 4,877,738 A | 10/1989 | Handelsman et al. | 435/252.5 |
| 4,891,319 A | 1/1990 | Roser | 435/188 |
| 5,049,379 A | 9/1991 | Handelsman et al. | 424/115 |
| 5,429,828 A | 7/1995 | Fodge et al. | 426/18 |

FOREIGN PATENT DOCUMENTS

| | | |
|---|---|---|
| EP | 0 477 739 A2 | 4/1992 |
| EP | 0743017 A2 * | 11/1996 |
| JP | 55-34039 | 10/1980 |
| WO | 97/41739 | 11/1997 |
| WO | 00/21381 | 10/1999 |

OTHER PUBLICATIONS

Collins et al., "Scale–Up of a Chiral Resolution Using Cross–Liinked Enzyme Crystals," American Chemical Society and Royal Society of Chemistry, vol. 2, No. 6, pp. 400–406 (1998).

B. Roser, "Trehalose Drying: A Novel Replacement for Freeze–Drying," BioPharm, pp. 47–53 (1991).

Kuppe, A., "Phosphatidylinositol–Specific Phospholipase C of *Bacillus cereus*: Cloning, Sequencing, and Relationship to Other Phospholipases", Journal of Bacteriology, Nov. 1989 pp. 6077–6083, (1989).

Barbis D. P. et al., "Characterization of Canine Parvovirus (CPV) Interactions with 3201 T–Cells: Involvement of GPI–Anchored Protein (s) in Binding and infection", Brazilian Journal of Medical And Biological Research, pp. 401–407, (1994), (abstract).

Gordon, V. M. et al.."*Clostridium septicum* Alpha Toxin Uses Glycosylphosphatidylinositol–Anchored Protein Receptors", Journal of Biological Chemistry, Sep. 17, 1999, vol. 274, No. 38, pp. 27274–27280, (1999).

Abraham et al., "Conservation of the D–Mannose–Adehesion Protein Among Type 1 Fimbriated Members of the Family Enterobacteriaceae," Nature 336: 682–684, 1988.

Adams, "Enzymes Are Important Components in Antibiotic–free Poultry Feeds," Feed Mix (Special 2000), pp. 16–18.

Aldridge, "Trehalose Boosts Prospects for Improved Biopharmaceuticals and Vaccines," Genetic Engineering News, pp. 10–11 (1995).

Arnold, F., "When Blind is Better: Protein Design by Evolution," Nature Biotechnol., vol. 16, pp. 617–618 (1998).

Arrowwood et al., "A New Method for Evaluating Experimental Cryptosporidial Parasite Loads Using Immunofluorescent Flow Cytometry," J. Parasitol, vol. 81, pp. 404–409 (1995).

Augustine, P., "Cellular Invasion by Avian Eimeria Species," Avian and Poultry Biology Review, vol. 11, pp. 113–122 (2000).

Barbis et al., "Characterization of Canine Parvovirus (CPV) Interactive with 3201 T Cells: Involvement of GPI––anchored Protein(s) in Binding and Infection," Brazilian J. Med. Biol. Res., vol. 27 , pp. 401–407 (1994).

Bergelson et al., "Decay–accelerating Factor (CD55), a Glycosylphosphatidylinositol–anchored Complement Regulatory Protein, is a Receptor for Several Echoviruses," Proc. Natl. Acad. Sci. USA, vol. 91, pp. 6245–6248 (1994).

Brantner, A., "Bewertung von Arzneibuchmethoden zur Bestimmung der Antimikrobiellen Wirksamkeit under Besonderer Berucksichtigung von Naturstoffen," Pharmazie, vol. 52, No. 1, pp. 34–40 (1997).

Cevallos et al., "Molecular Cloning and Expression of a Gene Encoding Cryptosporidium Parvum Glycoproteins gp40 and gp15," Infection and Immunity, vol. 68, No. 7, pp. 4108–4116 (2000).

Clarkson et al., "Characterization of the Echovirus 7 Receptor: Domains of CD55 Critical for Virus Binding," Journal of Virology, vol. 69, No. 9, pp. 5497–5501 (1995).

Colaco et al., "Extraordinary Stability of Enzymes Dried in Trehalose: Simplified Molecular Biology," Bio/Technology, vol. 10, pp. 1007–1011 (1992).

(List continued on next page.)

Primary Examiner—Manjunath Rao
(74) Attorney, Agent, or Firm—Foley & Lardner, LLP

(57) ABSTRACT

Enzymes of a particular class, characterized by the ability to cleave a linkage that effects release of a cell–surface protein or carbohydrate, which does not contain an anti-infection agent, display significant anti-infectious activity. Upon oral administration, these enzymes are effective, for example, in the treatment of digestive tract infections in humans and in animals. In the latter, there are benefits of significantly improved growth rate, feed efficiency, and overall health.

39 Claims, 1 Drawing Sheet

OTHER PUBLICATIONS

Cherry et al., "Directed Evolution of a Fungal Peroxidase," Nature Biotechnology, vol. 17, pp. 379–384 (1999).

Crameri et al., "DNA Shuffling of a Family of Genes from Diverse Species Accelerates Directed Evolution," Nature, vol. 391, pp. 288–291 (1998).

Essen et al., "Crystal Structure of a Mammalian Phosphoinositide–specific Phospholipase Cδ," Nature, vol. 380, pp. 595–602 (1996).

Essen et al., "A ternary Metal Binding Site in the C2 Domain of Phosphoinositide–Specific Phospholipase C–δ1," Biochemistry, vol. 36, pp. 2753–2762 (1997).

Fodge et al., "Post–pelleting Application of Heat–labile Products Explored," Feedstuffs, vol. 29, No. 40, pp. 1–7 (1997).

Franks et al., "Materials Science and the Production of Shelf–Stable Biologicals," Bio Pharm, vol. 4, No. 9, pp. 38, 40–42 and 55 (1991).

Friedman et al., "Specific Inhibition of Virus Growth in Cells Treated with Phospholipase C," Proc. NAS, vol. 59, pp. 1371–1378 (1968).

Gilmore et al., "*Bacillus cereus* Cytolytic Determinant, Cereolysin AB, Which Comprises the Phospholipase C and Sphingomyelinase Genes: Nucleotide Sequence and Genetic Linkage," Journal of Bacteriology, vol. 171, No. 2, pp. 744–753 (1989).

Giver et al., "Directed Evolution of a Thermostable Esterase," Proc. Natl. Acad. Sci. USA, vol. 95, pp. 12809–12813 (1998).

Gurnett et al., "A Family of Glycolipid Linked Proteins in *Eimeria tenella*," Molecular and Biochemical Parasitology, vol. 41, pp. 177–186 (1990).

Hawn et al, "Detection and Partial Characterization of Glycosylphosphatidylinositol–specific Phospholipase Activities from *Fasciola hepatica* and *Schistosoma mansoni*," Molecular and Biochemical Pharasitology, vol. 59, pp. 73–82 (1993).

Hendrickson et al., "A Fluorescent Substrate for the Assay of Phosphatidylinositol–Specific Phospholipase C: 4–(1–Pyreno)Butylphosphoryl–1–*myo*–Inositol," Bioorganic & Medicinal Chemistry Letters, vol. 1, No. 11, pp. 619–622 (1991).

Hendrickson, H.S., "Fluorescence–Based Assays of Lipaes, Phospholipases, and Other Lipolytic Enzymes," Analytical Biochemistry, vol. 219, pp. 1–8 (1994).

Hendrickson et al., "Kinetics of *Bacillus cereus* Phosphatidylinositol–Specific Phospholipase C with Thiophosphate and Fluorescent Analogs of Phosphatidylinositol," Biochemistry, vol. 31,, pp. 12169–12172 (1992).

Henry, C.M., "The Spector of Antibiotic Resistance Has Engaged Pharmaceutical and Biotechnology Companies to Seek New Weapons to Battle Infections," Science/Technology, vol. 78, No. 10, pp. 41–58 (2000).

Hogge, D. M., "Antibiotics and Their Alternatives for Poultry Examined," Feedstuffs, vol. 71, No. 20, pp. 1–7 (1999).

Ikezawa et al., "Studies on Phosphatidylinositol hosphodiesterase (Phospholipase C Type) of *Bacillus cereus*," Biochimica et Biophysica Acta, vol. 450, pp. 154–164 (1976).

Jacobs et al., "Dengue Virus Nonstructural Protein 1 is Expressed in a Glycosyl–phosphatidylinositol–linked Form That Is Capable of Signal Transduction," The FASEB Journal, vol. 14, pp. 1603–1610 (2000).

Karlsson, "Animal Glycosphingolipids As Membrane Attachment Sites for Bacteria," Annu. Rev. Biochem., vol. 58, pp. 309–350 (1989).

Kamogashira et al., "Isolation of Tunicamycin Produced by *Bacillus cereus* K–279," Gric. Biol. Chem., vol. 52, No. 3, pp. 859–861 (1988).

Karnauchow et al., "The HeLa Cell Receptor for Enterovirus 70 Is Decay–Accelerating Factor (CD55)," Journal of Virology, vol. 70, No. 8, pp. 5143–5152 (1996).

Kudo, S., "Enzymatic Basis for Protection of Fish Embryos by the Fertilization Envelope," Experentia 48, pp. 227–281 (1992).

Lanzrein et al., "GPI–anchored Diphtheria Toxin Receptor Allows Membrane Translocation of the Toxin Without Detectable Ion Channel Activity," The EMBO Journal, vol. 15, No. 4, pp. 725–734 (1996).

Liao et al., "Isolationof a Thermostable Enzyme Variant by Cloning and Selection in a Thermophile," Proc. Natl. Acad. Sci. USA, vol. 83, pp. 576–580 (1986).

Lovell–Badge, R., "A Freeze–Dryer and a Fertile Imagination," Nature Biotechnology, vol. 16, pp. 618–619 (1998).

Low et al., "Structural and Functional Roles of Glycosyl–Phosphatidylinositol in Membranes," Science, vol. 239, pp. 268–275 (1988).

Low et al., "Modification of Erythrocyte Membrances by a Purified Phosphatidylinositol–Specific Phospholipase C (*Staphylococcus aureus*)," Biochem. J., vol. 162, pp. 235–240 (1977).

Low, et al. "A Phospholipase D Specific for the Phosphatidylinositol Anchor of Cell–Surface Proteins is Abundant in Plasma," Proc. Natl. Acad. Sci. USA, vol. 85, pp. 980–984 (1988).

Malaviya et al., Proc. Natl. Acad. Sci. USA 96: 8110–8115 (1999).

McConville et al., "Structure, Biosynthesis and Function of Glycosylated Phosphatidylinositols in the Parasitic Protozoa and Higher Eukaryotes," Biochemical Journal, vol. 294, pp. 305–324 (1993).

Miller D.J.S., "Antibiotic Usages in Food Animal Production and Resistance—European Perspective," USAHA Proceedings (1999).

Muirhead S., "FDA/CVM Proposes to Withdraw Poultry Use of Fluoroquinolones," Feedstuffs, vol. 72, No. 45, pp. 1–4 (2000).

Nishihara et al., "Archaea Contain a Novel Diether Phosphoglycolipid with a Polar Head Group Identical to the Conserved Core of Eucaryal Glycosyl Phosphatidylinositol," The Journal of Biological Chemistry, vol. 267, No. 18, pp. 12432–12435 (1992).

Pearce et al., "Three Major Surface Antigens of *Schistosoma mansoni* Are Linked to the Membrane by Glycosylphosphatidylinositol," The Journal of Immunology, vol. 142, No. 3, pp. 979–984 (1989).

Roser B., "Trehalose Drying: A Novel Replacement for Freeze–Drying, " Biopharm, vol. 4, No. 8, pp. 47–53 (1991).

Rostand et al., "Cholesterol and Cholesterol Esters: Host Receptors for Psuedomonas Aeruginosa Adherence," The Journal of Biological Chemistry, vol. 268, No. 32, pp. 24053–24059 (1993).

Rygus et al., "Inducible High–level Expression of Heterologous Genes in *Bacillus megaterium* Using the Regulatory Elements of the Xylose–utilization Operon," Appl. Microbioo Biotechnol, vol. 35, pp. 594–599 (1991).

Rygus et al., "Molecular Clonging, Structure, Promoters and Regulatory Elements for Transcription of the *Bacillus megaterium* Encoded Regulon for Xylose Utilization," Arch Microbiol, vol. 155, pp. 535–542 (1991).

Sauma et al., "Selective Release of a Glycosylphosphatidylinositol–anchored Antigen from the Surfacre of *Shistosoma mansoni*," Molecular and Biochemical Parasitology, vol. 46, pp. 73–80 (1991).

Slein et al., "Partial Purification and Properties of Two Phospholipases of *Bacillus cereus*," vol. 85, pp. 369–381 (1963).

Slein et al., "Characterization of the Phospholipases of *Bacillus cereus* and Their Effects on Erythrocytes, Bone, and Kidney Cells," Journal of Bacteriology, vol. 90, No. 1, pp. 69–81 (1965).

Strong et al., "Cloning and Sequence Analysis of a Highly Polmorphic *Cryptosporidium parvum* Gene Encoding a 60–Kilodalton Glycoprotein and Characterization of Its 15– and 45–Kilodalton Zoite Surface Antigen Products," Infection and Immunity, vol. 68, No. 7, pp. 4117–4134 (2000).

Suszkiw, J., "Broiler Chicks May Benefit From "Spicer" Feed," USDA Agricult. Research Service, pp. 1–2 (1997).

Sylvester, et al., "Adherence to Lipids and Intestinal Mucin by a Recently Recognized Human Pathogen, Campylobacter Upsaliensis," Infection and Immunity, vol. 64, No. 10, pp. 4060–4066 (1996).

Tauguchi et al., "Phosphatidyl Inositol–Specific Phospholipase C from *Clostridium novyl* Type A," Archives of Biochemistry and Biophysics, vol. 186, No. 1, pp. 196–201 (1978).

Volwerk et al., "Phosphatidylinositol–Specific Phospholipase C From *Bacillus cereus*: Improved Purification, Amino Acid Composition, and Amino–Terminal Sequence," Journal of Cellular Biochemistry, vol. 39, pp. 315–325 (1989).

You et al., "A Chemiluminescence Immunoassay for Evaluation of *Cryptosporidium parvum* Growth in Vitro," FEMS Microbiol. Letters 136, pp. 251–256 (1996).

You et al., "In–vitro Activities of Paromomycin and Lasalocid Evaluated in Combination Against *Cryptosporidium parvum*," J. Antimicrobial Chemother, vol. 41, pp. 293–296 (1998).

Zhao et al., "Directed Evolution Converts Subtilisin E into Functional Equivalent of Thermitase," Protein Engineering, vol. 12, No. 1, pp. 47–53 (1999).

Zhao et al., "Molecular Evolution by Staggered Extension Process (StEP) in Vitro Recombination," Nature Biotechnology, vol. 16, pp. 258, 260 (1998).

Association of American Feed Control Officials Inc., Official Publication, "Drug and Feed Additives Section 30, Enzymes," pp. 224–335 (1999).

Baird & Tatlock (London) Ltd., Action of Phospholipase C on Influenza Virus, Nature, vol. 204, No. 4959, pp. 781–782 (1964).

Frost & Sullivan, "U.S. Pharmaceutical Products for Food––Animals Report," pp. 5245–5254 (1995).

Enzyme Nonmenclature, "Enzyme List," Academic Press (1992).

* cited by examiner

Anti-Cryptosporidial Activity of Recombinant PI-PLC Produced by Bacillus megaterium

SEQUENCE LISTING

<160> NUMBER OF SEQ ID NOS: 2

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 1
gactagtaat aagaagttaa ttttg    25

```
<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 2
cgggatccat attgttggtt attgg                                           25
```

ENZYME TREATMENT

CROSS-REFERENCE TO RELATED APPLICATIONS

This application claims the benefit of U.S. provisional patent application serial No. 60/169,935, filed on Dec. 10, 1999.

FIELD OF THE INVENTION

The present invention relates to a composition comprising and methodology for using enzymes, as anti-infection agents, in the context of treating or lowering the risk of digestive tract infections.

BACKGROUND OF THE INVENTION

In its 1998 Revision of the World Population Estimates and Projections, the United Nations Department of Economic and Social Affairs Population Division projected that the world population would reach 6 billion in 1999. The report also stated that it took only 12 years for the population to increase from 5 to 6 billion compared to 123 years to go from one to two billion. By the mid 21st century the projected population is between 7.3 and 10.7 billion. The remarkable population growth in the last decade is due partly to the efficient gains in food production resulting from the application of technology and intensive food production practices. For future growth, more efficiency gains in food production will be needed to keep pace.

One approach, which has made animal meat production more efficient, involves the widespread use of anti-microbial chemicals and antibiotics in animal feed. In large-scale farms, the spread of infection is very fast under the crowded production conditions. Widespread disease therefore is controlled by prophylactic and therapeutic uses of these substances. For example, it is common practice to incorporate chemicals in animal feeds to control coccidia infections (e.g., salinomycin, monensin, roxarsone (3-nitro), halquinol, carbadox and olaquindox) as well as anti-microbial antibiotics (e.g., bacitracin, virginiamycin, tylosin, tetracycline, chlortetracycline, penicillin, oleandomycin, novobiocin, lincomycin, bambermycins, apramycin, spiramycin, erythromycin, neomycin and others). This practice is well known to promote growth and improve feed conversion.

The rise in multiple antibiotic resistance among human pathogens, such as *Staphylococcus aureus, Streptococcus pneumoniae, Haemophilus influenza, Neisseria gonorrhoeae*, and *Mycobacterium tuberculosis*, has created fear that antibiotic resistance developed in microbes associated with farm animals could be migrating to human pathogens through transferable drug resistance factors. There is evidence that animals fed with antibiotics are a source of bacteria with transferable resistance factors. See Hooge, *Feedstuffs* 71(20):59, 1999. Although the antibiotics used in animals and in humans are generally different, there are similarities in mechanisms that could result in cross-resistance. In one case, fluroquinolones are approved for control of *E. coli* infections (colibacillosis) in some animals and also are used in human medicine. Hooge, supra. Recently the FDA/CVM has proposed to withdraw the approval to use the fluroquinolone enrofloxacin in poultry due to the development of fluoroquinolone-resistant campylobacter and transfer to humans. See Murhead, S. *Feedstuffs* 72(45):1–4, 2000.

There also is a concern among meat-producing industries that yield loss and possible resurgence of animal disease could occur if there is a ban on use of antibiotics and antimicrobials in feed. In 1986, for example, Sweden banned the use of feed antibiotics and animal disease increased. This was accompanied by an increased use of therapeutic antibiotics that resulted in an overall increase in the use of antibiotics as well as increased meat animal production costs. See Smith, *Feedstuffs* 71(13):1, 1999. In December 1998, the EU Council of Ministers decided to suspend the use of six antimicrobials that were formally approved as prescription-free in feed growth promoters (*Official Journal of the European Communities* 29.12.98, Council Regulation No. 2821/98 concerning Directive 70/524). Two quinoxaline-based additives were also banned in August 1999 due to concern about residues in the meat. The result of these actions is an increased prevalence of conditions formally suppressed including: necrotic enteritis in broilers; enteritis due to *Clostridium perfringens* in weaned pigs; swine dysentery and spirochaetal diarrhoea; and *E. coli*-associated diarrhoea. See Miller, *United States Animal Health Association*, 1999 Proceedings "Antibiotic Usages in Food Animal Production and Resistance-European Perspective."

There are 30,000 human deaths per year caused by nosocomial infections with resistant pathogens, but many fewer deaths from food borne pathogens. None of the deaths from food-borne pathogens have been linked to antibiotic resistance (see Smith, supra). Thus, it is not clear whether the use of antibiotics by the meat producing industries has contributed to the drug-resistant pathogen problem of the nosocomial infections in humans. Another concern is the lack of new antibiotics to treat infections with resistant pathogens. See Henry, C. M., *Chemical and Engineering News*, Mar. 6, 2000, pp 41–58. This could mean that when significant antibiotic resistant pathogens develop, there may be no new antibiotics available to treat the infections. The difficulty of developing antibiotics, market size, and regulatory issues seem to have caused the major pharmaceutical companies to move their R&D focus away from antibiotics development, especially for use in animals. New proposed regulations for registering a drug for animal use are so difficult that development is being stopped. See Smith, supra. There are, however, several small companies involved in the development of new antibiotics (Henry, supra).

In certain animal populations, infection is already pandemic. For example, avian coccidiosis is a disease that is only managed, but not really under control. Virtually all flocks are infected and anti-coccidiosis chemicals are commonly rotated in the feed to control damage and limit the development of resistant strains. Coccidiosis costs poultry producers $350 million annually in losses and medication expenses for antibiotic drugs such as salinomycin. See Suszkiw, *USDA Agricultural Research Service News*, Oct. 28, 1997. By 1999, it has been estimated that about $114 million would be spent annually on coccidiostats in the United States. See Frost & Sullivan, *U.S. Pharmaceutical Products for Food Animals*, Report 5245–54, 1995.

There is a clear need to find new and more effective methods to control infections in the digestive tract of animals that are grown using intensive farming practices. This need is based on a requirement to obtain better production efficiency in order to keep up with the rapidly expanding world population. Improved control of intestinal infection guarantees faster growth rate and improved feed efficiency. There is also a need for alternatives to antibiotic use in animal production to address the concern for possible antibiotic resistance development in human pathogens.

There is no risk of stimulating the evolution of resistant pathogenic microorganisms that present a problem for human health when using an enzyme-based treatment that operates in a manner different from all antibiotics. Since enzymes are proteins, there is no possibility that dangerous chemical residue will be incorporated in the meat products, as happens with some antibiotics and anti-coccidiosis chemicals. See American Feed Control Officials Inc., *Official Publication*, 1999, "Drugs and Feed Additives, Section 30.0 Enzymes," pp. 206–217, ISBN 1-878341-10-3.

SUMMARY OF THE INVENTION

It is therefore an object of the present invention to provide an enzymatic treatment to reduce the impact of digestive tract infections.

It is another object of the present invention to provide a mechanism to reduce the impact of digestive tract infections by interfering with the binding of pathogens to the cells of the digestive tract.

It is yet another object of the invention to provide an approach for increasing weight gain and feed conversion with respect to animals that are infected with pathogens which cause infections or necrotic enteritis.

It is a further object of the present invention to provide a dosage form, suitable for oral administration that is effective in improving the condition of a subject infected by or at risk of infection by a microbial pathogen.

In accomplishing these and other objects, there has also been provided, in accordance with one aspect of the present invention, a composition comprising (i) an enzyme that cleaves a linkage that effects release of a cell-surface protein or carbohydrate, the enzyme being other than an endo-1,4-D-mannanase, and (ii) a physiologically acceptable carrier for the enzyme, wherein the composition is in a form suitable for oral administration and contains no anti-infection agent other than the enzyme. In one embodiment, the enzyme in question cleaves a linkage that effects release of a cell-surface protein.

In a preferred embodiment, the enzyme included in the composition is a sphingomyelinase or a phospholipase, especially a type C or a type D phospholipase. In another preferred embodiment, the enzyme is selected from the group consisting of esterases, cerebrosidases, and carbohydrases that cleave a linkage that effects release of a cell-surface protein or carbohydrate. In another embodiment, the enzyme is prepared from a *Bacillus cereus* strain, preferably ATCC 7004 or ATCC 6464. Alternatively, the enzyme is obtained by expressing the recombinant DNA coding for the enzyme in *Bacillus megaterium*. In another embodiment, the enzyme is contained in a gelatin capsule shell and is present in the composition at 200 IU/Kg–4000 IU/Kg feed.

In accordance with another aspect of the present invention, a composition has been provided, having the aforementioned constituents (i) and (ii), wherein the physiologically acceptable carrier is a foodstuff into which the enzyme is incorporated. Thus, the composition can be an animal feed that contains no other anti-infection agent other than the enzyme. The animal feed composition of the present invention further comprises grain material, such as corn, sorghum, wheat, barley or oats, a source of protein, such as beans or peas, and vitamins, amino acids, and minerals.

In accordance with yet another of its aspects, the present invention provides a composition, as described above, that is in a solid or a liquid dosage form.

There is further provided a method of treating or ameliorating the risk of a digestive tract infection, comprising orally administering, to a subject suffering from or at risk for suffering the infection, an effective amount of enzyme that cleaves a linkage that effects release of a cell-surface protein or carbohydrate, wherein the enzyme is other than an endo-1,4-D-mannanase. In addition, the method does not include administering an anti-infection agent other than the enzyme itself. The infection may be affected by a protozoan, such as Eimeria and Cryptosporidium, bacterial, such as Clostridium, fungal or yeast pathogen.

There is even further provided a composition comprising (i) an enzyme that cleaves a linkage that effects release of a cell-surface protein or carbohydrate and (ii) a physiologically acceptable carrier for the enzyme, wherein the composition is in a form suitable for oral administration and does not contain an anti-infection agent other than the enzyme.

The is also further provided a method of treating or ameliorating the risk of a digestive tract infection, comprising orally administering, to a subject suffering from or at risk for suffering the infection, an effective amount of enzyme that cleaves a linkage that effects release of a cell-surface protein or carbohydrate, wherein the method does not include administering, with the enzyme, an antimicrobially effective amount of another anti-infection agent.

Other objects, features and advantages of the present invention will become apparent from the following detailed description. The detailed description and specific examples, while indicating preferred embodiments, are given for illustration only since various changes and modifications within the spirit and scope of the invention will become apparent to those skilled in the art from this detailed description. Further, the examples demonstrate the principle of the invention and cannot be expected to specifically illustrate the application of this invention to all the examples of infections where it will be obviously useful to those skilled in the prior art.

DETAILED DESCRIPTION OF THE INVENTION

Figure 1:
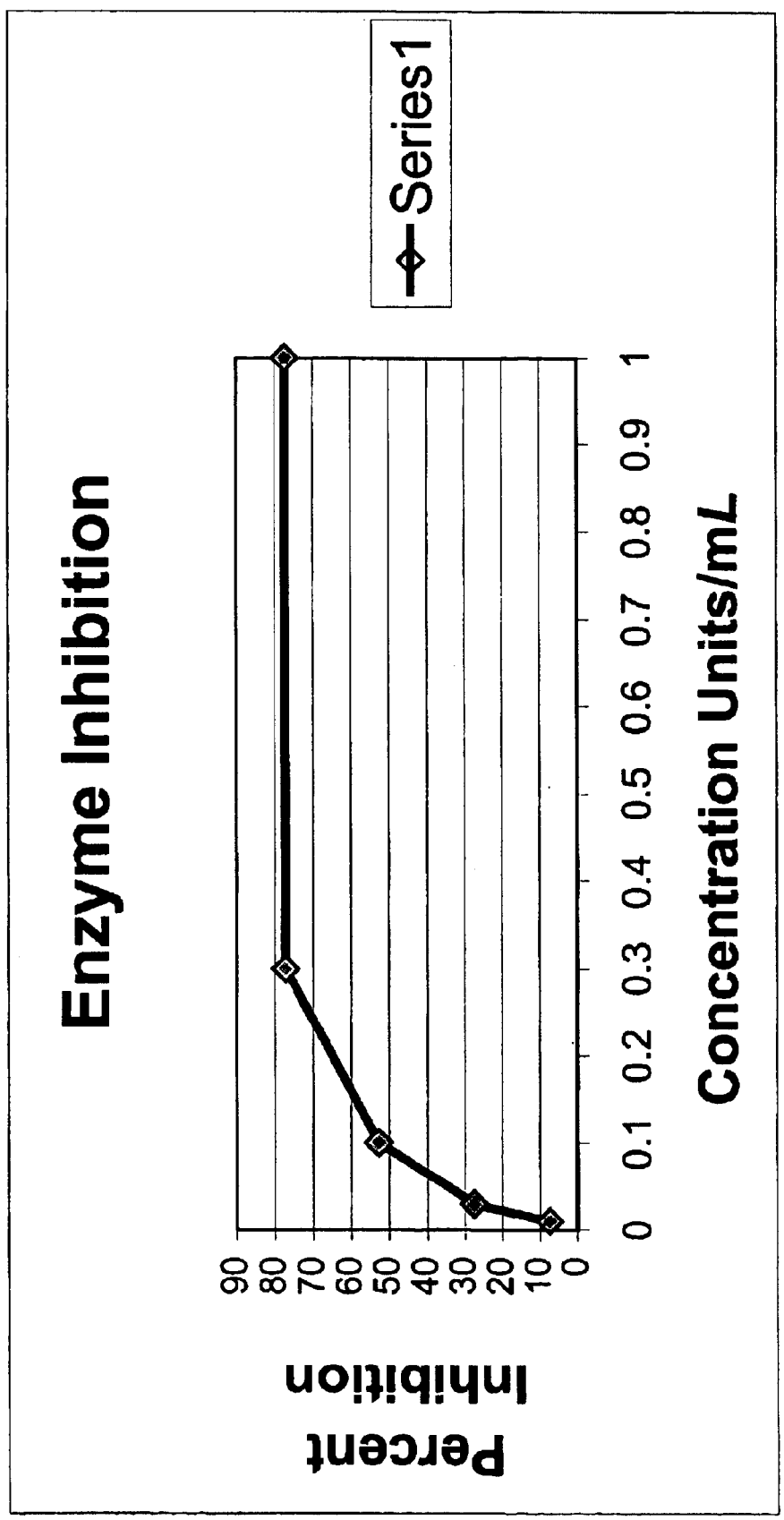
FIG. 1 shows the anti-cryptosporidial activity of the recombinant PI-PLC enzyme produced by a *Bacillus megaterium* strain.

It has been discovered that enzymes of a particular class, characterized by the ability to cleave a linkage that effects release of a cell-surface protein or carbohydrate, display significant antibiotic activity, upon oral administration, which is effective, for example, in the treatment of digestive tract infections. The enzyme class includes but is not limited to sphingomyelinases and phospholipases of type C and D, and enzymes of like cleavage specificity. Exemplary of this class, therefore, are enzymes that cleave and release glycoproteins or carbohydrates that are membrane-anchored via linkage to phosphatidylinositol. Thus, the enzyme phosphatidylinositol specific phospholipase C (E.C. 3.1.4.10), also known by the abbreviation PI-PLC or as 1-phosphatidylinositol phosphodiesterase, is a member of this class. Another example is glycosyl-phosphatidylinositol-specific phospholipase D, or GPI-PLD. Low and Prasad, *Proc. Natl. Acad. Sci.* 85:980–984, 1988.

The GPI-PLD and PI-PLC enzymes have been described from eukaryotic sources. See Low, "Degradation of glycosyl-phosphatidylinositol anchors by specific phospholipases", Chapter 2, pp 35–63, in Molecular and Cell Biology of Membrane Proteins: Glycolipid Anchors of Cell-Surface Proteins, A. J. Turner (ed.), Ellis Horwood, New York, 1990; Low and Prasad, *Proc. Natl. Acad. Sci.* 85:980–984, 1988; Essen et al., *Nature* 380:595–602, 1996; and Essen et al., *Biochemistry* 36:2753–2762, 1997. PI-PLC has been described from prokaryotic sources, including extracellular production by bacteria. Among the known bacterial sources of PI-PLC are *Bacillus cereus* (Stein and Logan, *J. Bacteriol.* 85:369–381, 1963; Stein and Logan, *J. Bacteriol.* 90:69–81, 1965; Ikezawa et al., *Biochimica et Biophysica Acta* 450:154–164, 1976; Griffith et al., *Methods in Enzymology* 197:493–502, 1991; Volwerk et al., *J. Cell. Biochem.* 39:315–325, 1989; and Kuppe et al., *J. Bacteriol.* 171:6077–6083, 1989), *Bacillus thuringiensis* (Ikezawa and Taguchi, *Methods in Enzymology* 71:731–741, 1981; Japanese patent document JP 55034039), *Staphylococcus aureus* (Low and Finean, *Biochem J.* 162:235–240, 1977), and *Clostridium novyi* (Taguchi and Ikezawa, *Arch. Biochem. Biophys.* 186:196–201, 1978).

Improved enzyme assay techniques for the PI-PLC enzyme have been devised based on a fluorescent substrate. See Hendrickson et al., *Biochemistry* 31:12169–12172, 1992; Hendrickson, *Anal. Biochem.* 219:1–8, 1994; Hendrickson et al., *Bioorg. Med. Chem. Letters.* 1:619–622, 1991.

Without ascribing definitively to any theory, the present inventors emphasize that PI-PLC enzyme has the ability to cleave the phosphatidylinositol glycolipid anchors of cell-surface proteins and other glycosyl phosphatidylinositols. See Low, supra; Low and Saltiel, *Science* 239:268–275, 1988. For example, the variant surface glycoproteins and other surface proteins and carbohydrates of several protozoan parasites are anchored by glycosyl phosphatidylinositol lipids (GPI anchors) and are sensitive to PI-PLC digestion and release. Illustrative species belong to the genera Schistosoma, Toxoplasma, Plasmodium, Trypanosoma, and Leishmania (Low, supra), as well as Eimeria, Babesia, Theileria, Giardia, Leptomonas and Entamoeba. See McConville and Ferguson, *Biochemical J.* 294:305–324, 1993; Pearce and Sher, *J. Immunol.* 142:979–984, 1989; Sauma et al., *Mol. Med. Biochem. Parasitol.* 46:73–80, 1991; Hawn and Strand, *Mol. Med. Biochem. Parasitol.* 59:73–82, 1993.

This anchoring mechanism for cell surface components appears to be universal for eukaryotic cells ranging from yeast to mammals. The presence of GPI anchors in *Giardia lamblia*, considered a very primitive eukaryote, suggests that this kind of anchor evolved early in the eukaryotes. Consistent with this understanding is the discovery, in the archaebacteria, of a new phosphoglycerolipid GlcNa1-6-myo-inositol-P-dialkylglycerol (Nishihara et al., *J. Biol. Chem.* 267:12432–12435, 1992), which is the base for the more complex eukaryotic GPI anchor structures that have evolved. In protozoa, the GPI anchorage system is used more heavily than in higher eukaryotes, and there is evidence that GPI-anchored structures are important for parasite survival in insect and mammalian hosts (McConville and Ferguson, supra). For example, the frequent shedding of variant surface glycoproteins may be a mechanism to avoid immune system attack.

The protozoan *Eimeria tenella* contains phosphatidylinositol-anchored structures similar to glycoprotein/glycolipid of *Trypanosoma brucei*. These are thought to be important for membrane attachment and subsequent infection. See Gurnett et al., *Mol. Med. Biochem. Parasitol.* 41:177–186, 1990. The Eimeria structures are cleaved by a trypanosome lipase and by *Bacillus thuringiensis* PI-PLC (Gurnett, supra). The in vivo treatment of parasites with PI-PLC, if proven feasible, likely would help the host immune system and interfere with attachment and infection by pathogens entering the digestive tract. Eimeria species are a widespread and costly problem for the poultry industry. Another protozoan parasite, *Cryptosporidium parvum*, is widespread and causes acute diarrheal disease in humans and many animals. The sporozoite protein, GP15/45/60, is predicted to be a GPI linked protein based on DNA sequence, and monoclonal antibodies reactive to this sporozoite protein inhibit infection (Strong, W. B., et al., *Infection and Immunity* 68:4117–4134, 2000; Cevallos, A. M., et al., *Infection and Immunity* 68:4108–4116, 2000). Thus, *C. parvum* is another pathogen potentially treatable with PI-PLC.

The prokaryotic bacteria do not contain surface glycoproteins and carbohydrates anchored by phosphatidylinositol (McConville and Ferguson, supra), but PI-PLC could still reduce bacterial infections by interfering with the attachment process. Pathogenic *E. coli* and a number of other well-known pathogenic Enterobacteriaceae expresses the bacterial adhesin FimH, a 29 kD mannose-binding lectin presented at the distal tip of fimbriae. Abraham et al., *Nature* 336:682–684, 1988. This adhesin has been shown to bind to CD48 of mast cells, a GPI-anchored molecule. See Malaviya et al., *Proc. Natl. Acad. Sci. USA* 96:8110–8115, 1999. In vitro digestion with PI-PLC reduced the binding of a mutant GPI-anchored diphtheria toxin (from *Corynebacterium diphtheria*) receptor to murine NIH3T3 cells. See Lanzrein et al., *EMBO J.* 15:725–734, 1996. In addition, *Clostridium septicum* alpha toxin and *Aeromonas hydrophila* aerolysin are both attached to the cell surface by means of a C-terminal GPI-anchor and can be removed from the cell surface by treatment with PI-PLC. See Gordon et al., *J Biol. Chem.* 274:27274–27280, 1999.

A mechanism for PI-PLC to reduce the effect of bacterial infection relates to the liberation of the CD48 binding site from the host mast cells. Also, the FimH binding to mast cells triggers an inflammation response. In accordance with the present invention, therefore, reducing the binding sites also should reduce inflammation, which could become excessive and damaging to intestinal health itself, as the inflammation response involves the release of tumor necrosis factor α (Malaviya, supra). Thus, via this mechanism of decreasing inflammation and the underlying secretion of tumor necrosis factor, a phospholipase treatment, according to the present invention, should relieve symptoms characterizing conditions such as irritable bowel syndrome, colitis, and Crohn's Disease. See van Deventer. S. J., *Ann. Rheum. Dis.* 58(1):I114–1120 (November 1999).

Against viral infections as well, the present invention should be effective, by its disruption of binding between viral particles and cells that the virus would infect in vivo. In light of the present inventors' discovery of the efficacy of oral administration, described herein, it is interesting that pretreatment of influenza virus with phospholipase C, causing the release of about 50% of the virus phospholipid, resulted in a significant decrease in infectivity in chick embryos. See Mizutani et al., *Nature* 204:781–782, 1964. Conversely, pretreatment of cultured chick embryo fibroblasts with phospholipase C, isolated from *Clostridium perfringens*, markedly inhibited subsequent infection of the cells by Semliki Forest Virus. See Friedman and Pastan, *Proc. Natl. Acad. Sci. USA* 59:1371–1378, 1968. While the art apprehended no therapeutic significance in these phenomena, in hindsight, they are consistent with one mechanism thought to underlie the present invention, namely, the cleavage of a pathogen-surface ligand and/or its cognate cell-membrane receptor, disturbing interaction that is necessary to infection.

Another way where the present invention may be effective in preventing viral infection is by abolishing the binding of viral GPI-anchored proteins to susceptible cells. An example of a viral GPI-anchored protein that is sensitive to PI-PLC digestion is Dengue Virus NS1 (nonstructural protein 1). See Jacobs et al., *FASEB J* 14:1603–1610, 2000. There are several examples of host cell GPI-anchored proteins that are the binding sites for viruses. These examples include human Echovirus 6,7,12 and 21 and Enterovirus 70 that bind GPI-anchored CD55 (decay-accelerating factor, DAF). See Clarkson et al., *J. Virology* 69:5497–5501, 1995; Bergelson, et al., *Proc. Natl. Acad. Sci. USA* 91:6245–6248, 1994; and Karnauchow, et al., *J. Virology* 70:5143–5152, 1996. Canine Parvovirus (CPV) infections can be blocked in vitro by pretreatment of feline cells with PI-PLC. See Barbis and Parrish, *Brazilian J. Med. Biol. Res.* 27:401–407, 1994.

Some cell surface receptors, of putative importance for initializing infections, are attached to membranes by mechanisms other than GPI anchors. These include structures such as cholesterol esters (Rostand and Esko, *J. Biol. Chem.* 268:24053–24059, 1993), the non-phosphorylated glycosphingolipids (Karlsson, *Ann Rev. Biochem* 58:309–350, 1989) and other phospholipids such as phosphatidylethanolamine and phosphatidylserine. See Sylvester, *Infect. Immun.* 64:4060–4066, 1996.

For the reasons stated above, therefore, targeting such structures with appropriate esterases, cerebrosidases, carbohydrases, and phospholipases active to release these structures from cell surfaces, should have beneficial effects, upon oral administration in accordance with the present invention, to treat digestive tract infections.

By virtue of the universal nature of phosphatidylinositol-linked surface proteins and carbohydrates in eukaryotes, the therapeutic methodology of the present invention, entailing the administration of enzyme, acutely or prophylactically, to cleave an anchoring linkage for such cell surface proteins and/or carbohydrates, will find broad application in managing protozoan, bacterial, fungal, and viral infections of the digestive tract. To this end, a key aspect of the present invention is the demonstration that an enzyme, which not only is active in cleaving cell surface components, can be administered orally as an anti-infection agent and be effective in vivo. Notably, while a representative suitable enzyme, PI-PLC, has been available since the 1960s, this approach has not been suggested heretofore.

Another aspect of the present invention is the use of an enzyme, as described above, as an effective anti-infection agent in animal feed preparations, which treat or ameliorate the risk of digestive tract infections in animals that consume the feed. Feed preparations that contain an endo-1,4-D-mannanase are known, and some reports have proposed an antifungal activity for mannanase. See WO 00/21381 (PCT/EP99/07835) and Kudo et al., *Experentia* 48:227–281, 1992. In these instances, mannanase is combined with a recognized antibiotic, although the prospect of enzyme use in antibiotic-free feed has been discussed generally. Adams, *Feed Mix* (Special 2000), at pages 16–18.

In one of its aspects, therefore, the present invention relates to compositions, including feed compositions, that contain an enzyme, characterized by above-mentioned cleaving activity, that is other than a mannanase or, more specifically, other than an endo-1,4- D-mannanase, as distinguished, for example, from a mannan-directed enzyme with a different cleavage specificity, as described in Enzyme Nomenclature 1992 (Academic Press) (see entries 3.2.1.77, 3.2.1.78, 3.2.1.101, 3.2.1.106, 3.2.1.130, and 3.2.1.137). Further, the present invention contemplates a composition that contains such an enzyme, including a mannanase, but that contains no other anti-infection agent.

Thus, in accordance with the present invention, an extracellular enzyme preparation, obtained from *Bacillus cereus* and standardized for PI-PLC content, can be used to bring about very significant improvement in weight gain and feed conversion in the presence of an infection. This result is unexpected because *B. cereus* is an opportunistic pathogen that commonly causes food-borne gastroenteritis and *B. cereus* endophthalmitis.

Early studies reported that injection of extracellular *B. anthracis* or *B. cereus* enzyme into rabbits causes phosphasemia and even death. For example, see Stein and Logan, *J. Bacteriol.* 85:369–381, 1963. It is surprising, therefore, that an extracellular enzyme from a pathogen which causes gastroenteritis would have a curative effect, pursuant to the present invention, in relation to a disease caused by a bacterial infection.

*Bacillus cereus* elaborates a variety of extracellular membrane-active enzymes and cytolytic toxins, including PI-PLC and Cereolysin AB, composed of phospholipase C and spingomyelinase. See Gilmore, *J. Bacteriol.* 171:744–753, 1989. In the aforementioned enzyme preparation, an extracellular phosphatidylinositol-specific phospholipase C [E.C. 3.1.4.10], produced by the *B. cereus*, is thought to be an active ingredient. Enzyme treatment of the present invention worked effectively as a coccidiostat and antibiotic. Therefore, it is an effective and commercially viable approach for the treatment of digestive tract infections particularly as currently used substances are banned.

If not coated, enzymes are capable of irreversible inactivation by gastric fluids of the stomach. U.S. Pat. No. 4,079,125 describes improved an enteric coated enzyme-containing compositions for ingestion by enzyme-deficient mammals. Surprisingly, addition of the PI-PLC to the animal feed without coating results in effective treatment of pathogenic infections.

Enzyme compositions according to the invention preferably are formulated as dried, solid or liquid oral compositions. Such compositions generally will include stabilizers, such as a buffer, a carbohydrate and/or a glycol. Dried, shelf-stable formulations of enzymes that are suitable, pursuant to the present invention, for incorporation in tablets or capsules, for example, can be prepared by freeze-drying, spray drying in fluidized bed dryer with inert or carbohydrate carrier, or by using evaporative techniques in conjunction with glass-forming stabilizers. See Franks et al., *Biopharm.* 4:38–55, 1991. Another approach involves salt precipitation, for example, ammonium sulfate precipitate or solvent precipitate, as with acetone for powder formation, followed by drying and blending with a carrier.

Certain carbohydrates, particularly monosaccharides, disaccharides, and lower oligosaccharides are important glass-forming carbohydrates. Exemplary carbohydrates for use as carriers are xylose, fructose, glucose, sorbitol and maltotriose, among others, as described by Franks, supra. Choice of a carbohydrate carrier is based on compatibility with the enzyme, low hydroscopic tendency, and a favorable glass transition curve. The stabilizer trehalose is particularly suitable for producing ambient temperature-stable biologics. See U.S. Pat. No. 4,891,319; Roser, *Biopharm.* 4 (8):47–53, 1991; Colaco et al., *Bio/Technology* 10:1007–1011, 1992; Aldridge, *Genetic Engineering News*, Mar. 15, 1995, pp 10–11.

Enzymes for the present invention can be formulated as liquids, for instance, as syrups with sorbitol or glycerol to lower water activity and stabilize the protein. Such solutions typically are sterile-filtered, prior to pharmaceutical use.

As previously noted, the present invention concerns, in one aspect, the delivery of enzyme as a component of feed or foodstuff. Feeds are composed mainly of grain material, a protein source, vitamins, amino acids, and minerals. The grain material typically includes corn, sorghum, wheat, barley, or oats. The source of proteins can be beans or peas, for example. Exemplary minerals, amino acids and vitamins include $B_{12}$, A, pantothenic acid, niacin, riboflavin, K, DL-methionine, L-lysine, choline chloride, folic acid, dicalcium phosphate, magnesium sulfonate, potassium sulfate, calcium carbonate, sodium chloride, sodium selenite, manganous oxide, calcium iodate, copper oxide, zinc oxide, and D-activated animal sterol.

For use in feeds, a liquid enzyme formulation can be prepared with salt water (e.g., NaCl, 15–18% w/w), or syrup to lower the water activity and to prevent microbial growth in the concentrated product. Other preservatives for feed such as sodium benzoate, propylparaben, sodium or potassium sorbate, and ascorbyl palmitate are examples of approved chemical preservatives that can also be used to prevent potential spoilage by microbial growth in the product. See Association of American Feed Control Officials, Inc., *Official Publication* 2000, Part 18, "Chemical Preservatives" pp 215–217, ISBN 1-878341-11-1. These preservatives can be applied to feeds by post-pelleting with a large dilution by automated spraying technology. See Fodge et al., *Feedstuffs*, Sep. 29, 1997. Such liquid preparations may contain stabilizing carbohydrates such as sorbitol or glycerol, if compatible. Materials that are desired components of feed, such as other enzymes or vitamins that are heat-labile, may be included for increased efficiency.

In instances where feed is utilized in a non-pelleted mash form (i.e., not heat-treated), enzymes for the present invention can be provided as a dry concentrate, for addition at the feed mixer. Such dry enzyme concentrates are prepared by first concentrating the liquid enzyme preparation, using a 10 Kd NMWC or other suitable ultra-filter, to achieve a high percentage of enzyme content, and then by blending with a very dry carrier, such as corn grits, soy grits or even an inert material or insoluble salt that is approved for use in feeds. See *Official Publication, American Feed Control Officials*, supra, Part 582, "Substances generally regarded as safe in animal feeds."

There are a number of techniques available for generating enzymes stable enough to tolerate the pelleting process in some feed mills, while retaining sufficient activity, at lower temperatures, to function in the digestive tract. It is well known that modifying protein structure, primarily through changing the encoding DNA sequence or, secondarily, through chemical modification can render enzymes more stable against inactivation. One illustration in this regard is the use of chemical cross-linking of enzyme crystals. See Collins et al., *Organic Process Research and Development* 2(6):400–406, 1998. Another approach to increasing the stability of enzyme for the present invention entails changing amino acids by mutagenesis of the gene that codes for the enzyme of interest, or obtaining genes or parts of genes for shuffling. See Crameri et al., *Nature* 391:288–291, 1998; Arnold, *Nature Biotechnol*. 16:617–618, 1998b; Zhao et al., *Nature Biotechnol*. 16:258–235, 1998; Zhao and Arnold, *Protein Eng*. 12:47–53, 1999. Mutation and selection for "directed evolution" of enzymes with the desired properties also is feasible. For example, see Giver et al., *Proc. Natl Acad. Sci. USA* 95:12809–12813,1998; Liao et al., *Proc. Nat'l Acad. Sci. USA* 83:576–580, 1986; Cherry et al., *Nature Biotechnol*. 17:379–384, 1999.

Certain protein modifications, including glycosylation, PEGylation and succinylation, also can enhance stability and alter pH optima, characteristics that could be optimized for enzyme to be used in the present invention. Thus, known protocols could be employed in this regard to make modified enzyme, for testing, according to the examples, to gauge suitability in the inventive treatment methodology.

An effective method for the production of PI-PLC arose from the cloning of the *B. cereus* gene into *B. megaterium*. The expression system (Rygus and Hillen, *Appl. Microbiol. Bacteriol.* 35:594–599, 1991) makes use of elements from the *Bacillus megaterium* xylose regulon (Rygus et al., *Arch. Microbiol.* 155:535–542, 1991), and was available commercially from BIO101 Corp. (Vista, Calif.). A fusion was created, between the PI-PLC gene leader coding sequence and the first three amino acids of *B. megaterium* xylA gene, in a plasmid stabilized with tetracycline resistance and regulated by a xylose responsive repressor. Strains of this type, with amplified expression, provide a feasible means for producing commercially useful amounts of PI-PLC, to incorporate into animal feed in accordance with the present invention.

Some *Bacillus cereus* isolates produce antibiotics such as tunicamycin. See Kamogashira et al., *Agric. Biol. Chem.* 52:859–861, 1988. Another isolate of *Bacillus cereus* (ATCC 53522) is described, in U.S. Pat. Nos. 4,877,738 and No. 5,049,379, as a biocontrol agent to prevent damping off and root rot in plants. This effect is believed to result from the action of two antibiotics, designated "Zwittennicin," a 396 Dalton linear aminopolyol, and "Antibiotic B," an aminoglycoside. In the examples detailed below, the possibility of involving these two antibiotics was eliminated by excluding possible low molecular-weight antibiotics from the enzyme preparation.

In particular, a cell-free fermentation broth was concentrated by means of a membrane with a 10 Kd molecular-weight cutoff. The concentrate, containing protein larger than 10 Kd, was used for further processing. The small molecular-weight antibiotics, such as those described by Handelsman, supra, would pass through this filter. Moreover, ammonium sulfate precipitation was employed to precipitate high molecular weight proteins, leaving low molecular weight materials in solution. After the ammonium sulfate precipitate was re-dissolved, the resultant enzyme solution was dialyzed against buffer, yet another treatment that removes low molecular-weight antibiotics. Finally, the protein was precipitated a second time, again with ammonium sulfate, to relegate any remaining, low molecular-weight compounds to the solution.

The combined use of these four treatments strongly militate against the possibility that the antibiotic effect observed is due to a low molecular-weight antibiotic, produced by ATCC 6464 or ATCC 7004. The fermentation broth also was tested, with an *E. coli* test strain, for the presence of antibiotic, but no antibiotic activity was detected.

The present invention is further described below by reference to the following illustrative examples.

EXAMPLE 1

Preparation of Frozen Stock Cultures of *Bacillus cereus* ATCC 6464 and ATCC 7004

Vials with lyophilized cells from the ATCC were opened and inoculated into a seed medium composed of Amberferm 4015 (Red Star) 10 g/L, Amberex 695 (Red Star) 5 g/L, and sodium chloride 5 g/L, pH 7.0 and grown at 30° C. The initial culture was streaked on LB Broth agar plates and a resulting single colony was inoculated back into 20 mL of seed medium in a 250 mL baffle flask (Bellco) and grown with shaking at 30° C. When the culture density reached $OD_{600}$ reading of 1.5, sterile glycerol was added to approximately 10% v/v and vials containing 1.8 mL of culture were frozen at –80° C.

EXAMPLE 2
Growth of ATCC 6464 and ATCC 7004 Isolates of *Bacillus cereus* for the Production of Phosphatidlyinositol Specific Phospholipase C Two Biostat C fermentors, 30 liters each, were batched with medium of the following composition, in tap water: Nutrient Broth No. 2 (Oxoid) at 25 g/L, Tryptone (Difco) at 10 g/L, yeast extract (Difco) at 10 g/L, and Mazu DP10P Mod11 antifoam (BASF) at 0.1 mL per liter. The initial batch volume was 9.5 L and the broth was sterilized at 121° C. for 40 minutes. The initial pH was adjusted to 7.0 with ammonia gas after sterilization.

Seed cultures were prepared in 500 mL of the same medium in 4-liter baffle shake flasks with aspirator connection (Bellco) with attached silicone tubing with connectors for inoculation. The flasks were sterilized in an autoclave at 121° C. for 50 minutes prior to inoculation with 1.8 mL of frozen stock culture prepared from the ATTC shipment (EXAMPLE 1). The seed flask cultures were grown at 30° C. for 5.5 hours with shaking at 200 RPM in a controlled environment incubator shaker (NBS model G-25). Prior to inoculation the ATCC 7004 culture had an $OD_{600}$ of 1.53 and pH 6.58. The ATCC 6464 culture had $OD_{600}$ of 1.28 and pH 6.79.

The 500 mL seed cultures were inoculated into the 30-L fermentors and operated under the following conditions: temperature 30° C., mixing RPM 600, air flow 10 liters per minute, and pressure 0.5 Bar. The $OD_{600}$ of the initial culture was 0.81. At six hours, the fermentation was stopped with final $OD_{600}$ of 22.1 (ATCC 7004) and $OD_{600}$ of 24.2 (ATCC 6464). The fermentations were run without pH control and the final pH was 8.17 (ATCC 7004) and pH 8.13 (ATCC 6464). Broth was removed from the fermentors and cooled to 8° C. prior to further processing.

The fermentors were run a second time using virtually an identical procedure with both ATCC *Bacillus cereus* isolates. In this case the seed cultures were used at six hours with $OD_{600}$ of 2.86 (ATCC 7004) and $OD_{600}$ of 1.98 (ATCC 6464), and a pH of 6.69 (ATCC 7004) and pH 6.65 (ATCC 6464). The main fermentations were run for 6.5 hours with final $OD_{600}$ of 35.9 (ATCC 7004) and $OD_{600}$ of 33.6 (ATCC 6464). Final pH was 8.38 (ATCC 7004) and pH 8.47 (ATCC 6464) at the time of cooling.

EXAMPLE 3

Cell Removal by Filtration and Concentration of PI-PLC Enzyme

Cells were removed and washed from each of the four fermentor batches described in EXAMPLE 2 using two A/G Technology (UFP-500-K-6A) 3 mm hollow fiber 500,000 molecular weight cut off (500 Kd NMWC) filters attached end to end. Chilled broth was pumped through the filters with a peristaltic pump at about 2 liters per minute with recycling back to the holding reservoir. The permeate containing the enzyme was collected in a reservoir chilled on ice. The initial cell-containing broth volume of about 9 liters was concentrated down to about 2 liters at which point diafiltation was started with 10 mM Tris-HCl, pH 8.5. After a total volume of about 14 liters of permeate was collected, the cell washing was terminated.

The 500 Kd permeate (about 14 liters from each fermentor) was concentrated with two A/G Technology (UFP-10-C-4XTCA) 0.5 mm hollow fiber 10,000 molecular weight cut-off filters (10 Kd) attached end to end. The same pumping method with recycle of concentrate was used except the permeate was discarded. Final concentrate with a volume of about 500 mL from each fermentor was saved for the next processing step.

EXAMPLE 4

Further Purification and Concentration of PI-PLC Enzyme

The 10 Kd ultrafilter concentrate (EXAMPLE 3) derived from each of the *Bacillus cereus* fermentations was adjusted to 80% saturation with ammonium sulfate and mixed on ice for 60 minutes. The solution was centrifuged for 15 minutes at 6000 RPM in a Sorvall GSA rotor. The supernatant was discarded, and the precipitate was dissolved in a minimal volume of 10 mM Tris-HCl, 0.2 mM EDTA (pH 7.5) and then dialyzed in the cold against the same buffer.

The protein in each concentrate was measured using a dye-binding assay (BioRad) and the level of PI-PLC was measured (Hendrickson et al., *Bioorg. Med. Chem. Letters* 1:619–622, 1991) using an HPLC based detection method and a fluorescent substrate (Molecular Probes, Inc., P-3764, 1-pyrenebutyl myo-inositol-1-phosphate, lithium salt). Table 1 below summarizes the assay data and predicts the approximate purity and total enzyme on a pure basis obtained for each of the four preparations. The enzyme preparations were stored frozen at −20° C. until further processing.

TABLE 1

Summary of Analysis of PI-PLC Crude Enzyme Preparations

| Enzyme Prep. | ATCC Strain Number | Protein mg/L | Specific Activity U/mg[1] | Total mg protein in preparation | Estimated % Purity[2] | Total mg PI-PLC on pure basis |
|---|---|---|---|---|---|---|
| 1 | 7004 | 1.86 | 1.75 | 325 | 2.92 | 9.49 |
| 2 | 6464 | 1.44 | 0.52 | 345 | 0.867 | 2.99 |
| 3 | 7004 | 1.35 | 4.42 | 208 | 7.36 | 15.3 |
| 4 | 6464 | 2.06 | 1.72 | 256 | 1.95 | 5.00 |

[1]U = unit = 1 micromole/minute.
[2]Based on the assumption that 100% pure protein has a specific activity of 60 U/mg (Hendrickson, supra).

EXAMPLE 5

Pooling and Concentration of Enzyme Preparations Prior to Application to Animal Feed The enzyme preparations 1, 2, 3 and 4 were pooled with a total volume of 675 mL. Ammonium sulfate (492 g) was added slowly and the solution was mixed on ice for several minutes. The solution was centrifuged to collect the precipitate. The pellet fraction was dissolved in a minimal amount of 20 mM phosphate buffer (pH 7.0).

The resulting solution was 70.9 mL with a density of 1.057 grams/cc. The protein concentration was measured at approximately 25.5 mg/mL. The PI-PLC activity was measured at approximately 1.13 U/mg with an estimated purity of the PI-PLC at 1.88%. The solution was frozen at −20° C. in its entirety, and was thawed and used to uniformly treat 200 pounds of chicken feed.

EXAMPLE 6

Cloning and Expression of *Bacillus cereus* PI-PLC Gene in *Bacillus megaterium*

The gene coding for phosphatidylinositol specific phospholipase C (PI-PLC) has been sequenced. See Kuppe et al., *J. Bacterial.* 171:6077–6083, 1989. Using PCR technology, the PI-PLC gene was cloned from *Bacillus cereus* (ATCC 6464) chromosomal DNA. An expression vector, pMEGA (BIO 101, Vista, Calif.), for *Bacillus megaterium* was used. Two PCR primers, 5'-GACTAGTAATAAGAAGTTAATTTTG-3' (primer 1; SEQ ID NO:1) and 5'-CGGGATCCATATTGTTGGTTATTGG-3' (primer 2; SEQ ID NO:2), were designed with a SpeI site in primer-1 (SEQ ID NO:1) and a BamHI site in primer-2 (SEQ ID NO:2).

The PCR-amplified PI-PLC gene was ligated into the pMEGA SpeI-BamHI site and yielded a plasmid pCG682. PI-PLC protein was fused with the first three amino acids of xylA gene product at the SpeI site in the expression vector. The expression of the PI-PLC gene was under the regulation of xylA promoter. The shake flask fermentation was used to evaluate the phosphatidylinositol specific phospholipase C production in *Bacillus megaterium*. LB broth with 10 μg/mL tetracycline (20 mL) was inoculated with 0.2 mL of seed culture and incubated in a 37° C. shaker at 250 rpm. At $OD_{600}$ of about 0.5, 5 g/L of D-(+)-xylose was added to induce the xylA promoter. After three hours, supernatant was harvested by centrifugation. The phosphatidylinositol-specific phospholipase C activity was measured by a fluorescent substrate method (Hendrickson, et al., *Biochemistry* 31:12169–12172, 1992; Hendrickson, *Anal. Biochem.* 219:1–8, 1994), using 1-pyrenebutyl-myo-inositol-1-phosphate substrate (Molecular Probes, Eugene, Oreg.) and by HPLC detection.

TABLE 2

Measurement of PI-PLC Expression

| Test Material | Xylose addition | Specific activity (unit/mg protein) |
|---|---|---|
| Cell Lysate Fractions | | |
| B. megaterium/pCG682 | – | 0 |
| B. megaterium/pCG682 | + | 0.436 |
| B. megaterium/pCG682 | – | 0 |
| B. megaterium/pCG682 | + | 0.365 |
| Fermentation Broth Fractions | | |
| B. megaterium/pCG682 | – | 0 |
| B. megaterium/pCG682 | + | 4.087 |
| B. megaterium/pCG682 | – | 0 |
| B. megaterium/pCG682 | + | 4.56 |

These data show that most of the PI-PLC is extracellular and that expression occurs only after D(+)xylose addition (Table 2). This recombinant strain is estimated to have at least 15 times the productivity (mg/L/OD) of the average wild strain, as grown in EXAMPLE 2.

EXAMPLE 7

Fermentation of *B. megaterium* for PI-PLC Production

The *B. megaterium*/pCG682 described in Example 6 was used for production of PI-PLC by fermentation. The medium (PM) for the seed and fermentation stages contained 20 g/L Amberferm 4015 (Universal Flavors Bionutrients, Indianapolis, Ind.), 10 g/L Amberex 695 yeast extract (Universal Flavors Bionutrients, Indianapolis, Ind.), 10 g/L NZ Case Plus (Quest International, Hoffman Estates, Ill.), 2.0 g/L $K_2HPO_4$, 0.1 g/L MgSO4.7$H_2O$ and 2.0 g/L glucose initially and 12.5 mg/L tetracycline. The pH was adjusted to 7.5.

Seed stage (500 mL in a 2.8-L baffle flask) was initiated by inoculation from a frozen seed vial and shaking at 250 RPM at 30° C. Seed vials were prepared by adding a single colony grown on an LB agar plate into 20 mL PM in a 250 mL shake flask. After growth to about 1.0 $OD_{600}$ at 30° C., 5 mL of 50% sterile glycerol was added, mixed and the solution was distributed into 2 mL plastic sterile vials and frozen at –60° C.

The 500 mL seed flasks were used after growth to about 1.2 to 1.8 $OD_{600}$ nm after 9 hours of shaking. Two flasks were used to seed a 60-L fermentor filled with 50-L of the same steam sterilized medium. Tetracycline was sterile filtered (0.2 micron filter) as a 1% solution in 40% ethanol and added after sterilization and cooling to 30° C. In fermentors, 0.1 mL/L of Mazu DF100PMOD11 antifoam (BASF, Gurnee, Ill.) was also added in the initial batch and added as needed to control foam during the fermentations. The operating conditions for the first fermentor seed stage were as follows: pressure 0.5 to 2.5 psig; temperature 30° C.±0.5° C.; agitation 200 to 450 RPM; air sparge 25 to 50 SLPM; dissolved oxygen ≧25%. The pH was controlled at 6.9 to 8.1 using 21.25% $H_3PO_4$ or 5N NaOH. When the $O.D_{600}$ reached 8–10, the contents were used to seed a 600-L fermentor containing 425 L of the same medium.

The operating conditions for the 600-L production fermentor were as follows: pressure 0.5 to 2.5 psig; temperature 30° C.±0.5° C.; agitation 100 to 300 RPM; air sparge 250 to 500 SLPM; dissolved oxygen >25%. The pH was controlled at 6.9 to 8.1 using 21.25% $H_3PO_4$ or 5N NaOH. When the initial glucose was exhausted at 5 hours and $OD_{600}$ of about 17, a xylose feed (pre-sterilized by autoclave at 121° C. for 20 minutes and composed of 10 kg D-(+)-xylose and 10 liters of water) was initiated. D-Xylose was obtained from Varsal Instruments, N.J. The feed was initially started at 25 mL/minute and held for 1.5 hour, then increased to 43 mL/minute. The second rate was held until all 22.5 liters of the xylose feed had been consumed. The dissolved oxygen was maintained by increasing the sparge air by 50 SLPM increments up to 500 SLPM. Once the airflow was at 500 SLPM, then the RPM was increased. The fermentation was terminated at 20 hours. By 17 hours, 7440 U/L (units as defined by Example 4) had accumulated.

The fermentation broth was harvested using a Pall Filtron C10 Skid and four CellFlo Microgon modules (0.2 μm membrane pore, 1 mm diameter fibers with 3.3 $m^2$). The 0.2 μm membrane permeate was concentrated using a LT100 Pall Filtron Skid with an AG/Technologies Size 85 10K ultrafiltration membrane. The final concentrate was 10 liters in volume and was frozen at –20° C.

EXAMPLE 8

*Bacillus cereus* Fermentation Broth did not contain Antibiotic Activity

Fermentation with *Bacillus cereus* (ATCC 7004) was conducted according to the method described in EXAMPLE 2 except that the initial volume was increased to 20 liters. A test for the presence of antibiotic was conducted with *E. coli* MG1655 as the testing strain with final fermentation broth or partially purified PI-PLC prepared according to the method described in EXAMPLES 3–5. The test was conducted as a cylinder plate assay. See Brantner, *Pharmazie* 52(1):34–40, 1997. No clearing zone indicating antibiotic activity was observed around the cylinders containing the enzyme samples.

EXAMPLE 9

PI-PLC Assay with Microtiter Plate Fluorescence Assay

An improved biochemical test for PI-PLC over the method of Hendrickson et al. (supra) used in Example 4 was developed. The substrate 4-methylumbelliferyl-myo-inositol-1-phosphate, N-methyl-morpholine salt was obtained from Biosynth (Naperville, Ill.). Reactions were monitored in a Flouroscan II fluorescence micro-titer plate reader obtained from MTX Lab Systems (Vienna, Va.). For assays of fermentation broth or enzyme concentrates, reactions of 200 µL were performed in black plastic micro-titer plates composed of 10 mM Tris-Cl, 0.16% deoxycholate, 0.8 mM 4-methylumbelliferyl-myo-inositol-1-phosphate, N-methyl-morpholine salt, and diluted enzyme at pH 8.0. Enzyme dilutions if needed are made into 0.1% BSA solution in water. The reaction was followed at 37° C. for 30 minutes reading at 2-minute intervals to observe the release of methylumbelliferone from the substrate with excitation at 350 nm and emission at 450 nm.

The correlation of fluorescence units to micromoles of methylumbelliferone is used to calculate the units (micromoles per minute) formed per amount of enzyme solution added. The reaction at pH 8.0 is a compromise between the pH optimal for the enzyme and the pH for maximal fluorescence of methylumbelliferone (pH 10). Also, at pH 9.0 and above, the rate of non-enzymatic release of methylumbelliferone becomes significant. Under this assay condition, the specific activity (units/mg) is about 39.3-fold higher than when using the Hendrickson et al. (supra) method. For the purpose of efficacy testing in animal feeding experiments, the units measured using this assay were converted to the equivalent Hendrickson Unit to facilitate comparison with the first tests before this assay was used.

EXAMPLE 10

Assay of PI-PLC added at Effective Doses in Animal Feeds

A more sensitive variation of the 4-methylumbelliferyl myo-inositol-1-phosphate, N-methyl-morpholine salt based assay of PI-PLC (Example 9) was devised for measuring enzyme after addition to animal feed that involves one pH for assay, and another pH for measuring fluorescence. The enzyme was extracted from feed test materials by weighing 4 g feed and adding it to 20 mL of 10 mM Tris-Cl (pH 7.5) with 0.1% deoxycholate to make 20 g/L feed. The slurry was shaken in a NBS G-25 shaker (New Brunswick Scientific) for 1 hour at room temp at 250 RPM. The slurry was centrifuged at 13,000 RPM in an IEC Micromax microcentrifuge with 1.5 mL microcentrifuge tubes. Appropriate dilutions of the extracts were made in 0.1% BSA (bovine serum albumin). Samples extracted from feeds with the application of 10 U/lb were not diluted.

First Reaction Step

Tubes were set up as follows. Standards at 1:100 or 1:200 dilution of 0.12 U/mL PI-PLC (unit defined as in Example 4) and a blank should also be included. Sample reactions should be foil-covered to protect the substrate from light.

| |
|---|
| 20 µL Tris-Hcl, 0.10M, pH 6.0 |
| 40 µL Deoxycholate (0.8%) |
| 40 µL PI-PLC substrate (4 mM) |
| 100 µL of enzyme |
| 200 µL/tube Total React at 25° C. |

Two time points were taken (30 min and 60 min) by the removal of 0.10 mL of each reaction. Aliquots were heated at 65° C. for 15 minutes to stop enzyme reaction and cooled on ice. Finally, samples were centrifuged at 12,000 RPM in a microcentrifuge for 5 minutes.

Fluorometer Reading

120 µL of 0.10 M Tris buffer (pH 8.0) Tris buffer was added to a microtiter well in a black plastic plate, then 80 µL of the reaction sample was added before reading as described in Example 7. Background control levels were subtracted. A rate of fluorescence units production per minute was calculated. Fluorescense units were converted to micromoles of reaction product and enzyme units extracted per original pound of feed was calculated.

EXAMPLE 11

Chicken Feeding Trials with Pathogen Challenge

I. Broiler Chicken Feeding Trial I

A first feeding trial starting with one-day old male broiler chickens was performed. A typical uniform chicken feed diet of "starter feed," designed to meet or exceed the National Research Council's Nutrient Requirements for Poultry ($9^{th}$ ed., 1994), was prepared and fed in mash form. The chickens were divided in cages (12 inches×24 inches floor space) in four treatment groups with each treatment group repeated four times and six birds per cage repeat (TABLE 3). Water and feed were provided ad libitum throughout the 21 day test period. A randomized block design was used to allocate chicks to cages and cages to treatment groups. All cages, feeders and waterers were sanitized prior to the beginning of the test. Lighting was continuous (24 hour per day) with incandescent lamps. Body weights were determined at day one and 21-day. Feed consumption was measured at day 21.

At day 5, all the chickens were infected with 200,000 oocysts per bird of Eimeria acervulina by oral gavage. On day 7, all birds were further infected with 500,000 Clostridium perfringens through the water supply. In the negative control (T1) there was no treatment for infection. In the positive control (T2) a coccidiostat and antibiotic were added to the feed. This was the anti-coccidiosis treatment Sacox (salinomycin at 60 g/ton) and the antibiotic BMD-50 (50 g/ton). For treatment groups, T3 and T4, the wild type PI-PLC enzyme treated feed (about 0.34 grams PI-PLC on a pure basis) was used beginning at day five at the time of the oral gavage with Eimeria acervulina. All the feed was prepared in one uniform batch, then divided for addition of antibiotic (Test Group T2) or enzyme (Test Groups T3 and T4). Results of bird weight analysis are presented in Table 4 and feed/gain calculations are presented in Table 5.

TABLE 3

Experimental Treatment for Broiler Chicken Feeding Trial I

| Test Group # | Test Description | Test Material | Replications | Chicks per replication |
|---|---|---|---|---|
| T1 | Negative Control | None | 4 | 6 |
| T2 | Positive Control | Coccidiostat and salinomycin treatment | 4 | 6 |
| T3 | PI-PLC Wild type | 0.34 g enzyme/ton (pure basis) | 4 | 6 |
| T4 | PI-PLC Wild type | 0.34 g enzyme/ton (pure basis) | 4 | 6 |

TABLE 4

Average Body Weight (g) at 21 Days

| | Treatment | | | |
|---|---|---|---|---|
| Rep | T1 | T2 | T3 | T4 |
| 1 | 323.00 | 341.67 | 377.83 | 366.67 |
| 2 | 326.67 | 321.33 | 383.83 | 361.17 |
| 3 | 299.33 | 337.33 | 378.83 | 361.33 |

TABLE 4-continued

Average Body Weight (g) at 21 Days

| | Treatment | | | |
|---|---|---|---|---|
| Rep | T1 | T2 | T3 | T4 |
| 4 | 211.67 | 254.00 | 374.33 | 403.40 |
| Mean | 290.17 | 313.58 | 378.71 | 373.14 |
| STAT | b | b | a | a |
| S.D. | 46.52 | 35.22 | 3.40 | 17.61 |
| C.V. | 16.03 | 11.23 | 0.90 | 4.72 |

TABLE 5

Average Feed Conversion (0–21 days)
Corrected for Weight of Mortality Birds

| | Treatment | | | |
|---|---|---|---|---|
| Rep | T1 | T2 | T3 | T4 |
| 1 | 1.486 | 1.569 | 1.407 | 1.445 |
| 2 | 1.562 | 1.532 | 1.423 | 1.421 |
| 3 | 1.524 | 1.562 | 1.432 | 1.406 |
| 4 | 1.760 | 1.462 | 1.438 | 1.404 |
| Mean | 1.583 | 1.531 | 1.425 | 1.419 |
| STAT | b | b | a | a |
| S.D. | 0.11 | 0.04 | 0.01 | 0.02 |
| C.V. | 6.68 | 2.78 | 0.82 | 1.17 |

In both of the foregoing tables, means in a row without a common letter are significantly different (P < 0.05), per Duncan's test for significance.

II. Broiler Chicken Feeding Trial II

A second feeding trial starting with one-day old male broiler chickens was conducted. The basal diets were designed to exceed the National Research Council's Nutrient Requirements for Poultry ($9^{th}$ Ed., 1994) and were prepared in mash form to ensure uniformity. The study was done in randomized battery cages, on a blinded basis, to test the effect of PI-PLC made from the natural source, *Bacillus cereus* (wild type PI-PLC), or a recombinant *Bacillus megaterium* on male broiler performance reared to 21 days of age. The natural source also contains other extracellular enzymes but the PI-PLC prepared from *Bacillus megaterium* is highly purified and was further purified by ultrafiltration using a 30-Kd NMWC membrane. Birds were challenged at 8 days of age with Avian coccidia (200,000 *E. acervulina* oocysts per bird via drinking water) and at 10 days of age with *Clostridium perfringens* (100,000 per bird via drinking water). Each of the nine treatments (Table 6) had 10 replications or cages. Each cage contained 6 vaccinated (Newcastle-Bronchitis, Mareks) Cobb×Cobb male broilers with a spacing of 0.40 $ft^2$/bird. Dead birds, if present, were not replaced after the $8^{th}$ day. Feed was fed in mash form on an ad libitum basis throughout the entire trial test period (day 0 to day 21).

A common and untreated basal mash diet, not containing antibiotics, was fed to all birds from days 0 to 7. Thereafter, nine treated diets, in mash form, were fed from 8–21 days of age. The basal feed was a typical broiler starter feed containing 22% crude protein, with an ME (metabolizable energy content) of 1400 kcal/lb.

TABLE 6

Experimental Treatment for Broiler Chicken Feeding Trial II

| Treatment | Test Article | Infection Challenge[1] |
|---|---|---|
| T1 | NONE | + |
| T2 | Bacitracin methylene disalicylate (BMD, 50 g/ton) and Salinomycin (Sacox, 60 g/ton) | + |
| T3 | Recombinant PI-PLC (3 U/lb) produced by *Bacillus megaterium* | + |
| T4 | Recombinant PI-PLC (10 U/lb) produced by *Bacillus megaterium* | + |
| T5 | Recombinant PI-PLC (30 U/lb) produced by *Bacillus megaterium* | + |
| T6 | Recombinant PI-PLC (90 U/lb) produced by *Bacillus megaterium* | + |
| T7 | PI-PLC (10 U/lb) and other extracellular enzymes from *Bacillus cereus* | + |
| T8 | NONE | NONE |
| T9 | Recombinant PI-PLC (90 U/lb) produced by *Bacillus megaterium* | NONE |

[1]200,000 *E. acervulina* oocysts were administered per bird via drinking water at 7 days, and at 10 days of age with 100,000 *Clostridium perfringens* bacteria per bird via drinking water.

TABLE 7

Broiler Chicken Feeding Trial II

| Treatment | 1 | 2 | 3 | 4 | 5 | 6 | 7 | 8 | 9 |
|---|---|---|---|---|---|---|---|---|---|
| Infection | + | + | + | + | + | + | + | − | − |
| Medication | − | + | − | − | − | − | − | − | − |
| PI-PLC Type | | | Rec[1] | Rec[1] | Rec[1] | Rec[1] | Wt[2] | | Rec[1] |
| Target U/lb | — | — | 3 | 10 | 30 | 90 | 10 | — | 90 |
| Ave Measured U/lb | 0.36 | 0.32 | 0.32[3] | 0.71 | 1.74 | 5.96 | 2.46 | 0.12 | 5.94 |
| 8–21 Day Weight Gain | 309.72 | 333.83 | 323.24 | 324.78 | 320.64 | 328.29 | 298.98 | 326.12 | 338.8 |
| | cd | ab | bc | ab | bc | ab | D | Ab | a |
| 8–21 Day Feed Conversion (Corrected) | 1.859 | 1.642 | 1.702 | 1.732 | 1.699 | 1.739 | 1.876 | 1.651 | 1.650 |

TABLE 7-continued

Broiler Chicken Feeding Trial II

| Treatment | 1 | 2 | 3 | 4 | 5 | 6 | 7 | 8 | 9 |
|---|---|---|---|---|---|---|---|---|---|
| | c | a | ab | b | ab | b | C | A | a |
| Average Intestinal Lesion Score | 1.447 | 0.833 | 1.120 | 1.133 | 0.842 | 0.808 | 1.267 | 0.983 | 0.847 |
| | d | A | bc | bc | a | a | Cd | ab | a |

[1]Recombinant PI-PLC produced by *Bacillus megaterium*.
[2]Wild type PI-PLC from *Bacillus cereus*.
[3]The addition level of PI-PLC was is too low to be effectively extracted and measured in this experiment and appeared as background level In the first trial when the bacterial infection was administered through the drinking water (Example 11-I,), by all criteria the wild type PI-PLC produced by *Bacillus cereus* worked as well as or better than the Salinomycin+BMD treatment (Tables 4–5). In a later test shown above with recombinant PI-PLC (Example 11-II, Table 7), PI-PLC added at varying concentrations, showed a dose-dependent effect on lowering the intestinal lesion score and feed conversion (T3–T6) and increasing weight gain. In addition, treatment with recombinant PI-PLC, at 90 U/lb, in the absence of the Salinomycin+BMD treatment, lowered the intestinal lesion score and had a positive effect on feed conversion and weight gain. Wild type PI-PLC from *Bacillus cereus* did not work as effectively as its recombinant counterpart at the same concentration (10 U/lb) in this test.

III. Broiler Chicken Feeding Trial III with Enymes, PI-PLC and endo-1,4-D-mannanase A study was performed in randomized Petersime battery cages to test the effect of PI-PLC and endo-1,4-D-mannanase (U.S. Pat. No. 5,429,828) on male broiler performance reared to 21 days of age. Birds were challenged at 8 days of age with avian coccidia (75,000 *E. acervulina* oocysts and 1,250 *E. maxima* oocysts per bird by oral gavage) and at 11, 12, and 13 days of age with *Clostridium perfringens* (oral gavage each day with 1 mL of fresh culture broth having $10^8$ cfu/mL). Each treatment (Table 8) consisted of 8 replications or cages and each cage housed 14 Mareks-vaccinated, Cobb×Cobb male broilers (reduced to 10 on Day 14 as 4 birds were removed from each cage and scored for lesions) with a spacing of 0.36 ft$^2$/bird. Dead birds were removed from the cages when they were detected and were not replaced. Feed was fed in MASH form on an ad libitum basis throughout the entire trial test period (day 0 to day 21).

Diets were fed in MASH form from 0–21 days of age. The basal feed was a typical broiler starter feed containing 22% crude protein, with an ME of 1400 kcal/lb.

TABLE 8

Experimental Treatments with Broiler Chicken Feeding Trial III

| Treatment | Medication[1] | Infection Challenge[3] | PI-PLC | Mannanase[2] |
|---|---|---|---|---|
| 1 | + | − | — | — |
| 2 | + | − | — | 100 MU/T |
| 3 | − | + | — | — |
| 4 | − | + | — | 100 MU/T |
| 5 | − | + | Wildtype PT-PLC (10 U/lb) produced by *Bacillus cereus* | — |
| 6 | − | + | Recombinant PI-PLC (30 U/lb) produced by *Bacillus megaterium* | — |
| 7 | − | + | Recombinant PI-PLC (10 U/lb) produced by *Bacillus megaterium* | 100 MU/T |
| 8 | − | + | Recombinant PI-PLC (30 U/lb) produced by *Bacillus megaterium* | 100 MU/T |
| 9 | + | + | — | — |
| 10 | + | + | Recombinant PI-PLC (30 U/lb) produced by *Bacillus megaterium* | — |

[1]The diet contained bacitracin methylene disalicylate (BMD, 50 g/ton) and salinomycin (Sacox, 60 g/ton).
[2]100 MU/T is equal to $100 \times 10^6$ units of activity per ton of feed.
[3]Birds were challenged at 8 days of age with 75,000 *E. acervulina* oocysts and 1,250 *E. maxima* oocysts per bird by oral gavage and at 11, 12, and 13 days of age with *Clostridium perfringens* by oral gavage each day with a fresh broth culture having $10^8$ cfu/ml.

Feed conversions were adjusted for differences in average bird weights for purposes of comparing the treatments. Infection worsened the AF/G (weight adjusted feed conversion) by about 23%. (0.147 AF/G units). The use of salinomycin and BMD completely restored the AF/G to normal levels, but these two chemicals were no better than the combination of −mannanase and PI-PLC in reducing the intestinal lesions caused by infection. One hundred million (100 MU) units −mannanase per ton either alone or in combination with PI-PLC partially overcame the deleterious consequences of infection as evidenced by the 65% to 70% improvement in AF/G reduction present in the infected control (see T3 v. T1). The −mannase appeared to lower the intestinal lesion score caused by *E. acervulina* more than of *E. maxima*. Partial restoration in AF/G was achieved in infected birds treated with PI-PLC in the feed, but only 33–41% of the worsening was overcome. However, both classes of PI-PLC lowered the intestinal lesion score caused by either Eimeria species. In the case of *E. maxima*, the lesion reduction was statistically significant. The results are shown in Table 9.

TABLE 9

Broiler Chicken Feeding Trial III with PI-PLC and endo-1,4--D-man n anase
fed to chickens infected with E. acervulina, E. maxima, and C. perfringens

| | Treatment Description | | | Feed Consumption | | Feed Conversion | | Weight Gain | | Live Wt. | Lesion Scores | | Weight AF/G[3] v. |
|---|---|---|---|---|---|---|---|---|---|---|---|---|---|
| | | β-man- | | Day | Day | Day | Day | Day | Day | Day | | | |
| | I[1] | M[2] | nanase | PI-PLC | 0–21 | 8–21 | 0–21 | 8–21 | 0–21 | 8–21 | 21 | E. acer. | E. max. | Treatment 1 |
| 1 | No | Yes | No | No | 11.178[ab] | 8.866[a] | 1.433[de] | 1.446[d] | 0.659[a] | 0.540a | 0.701[a] | 0.00[c] | 0.00[c] | 1.433 |
| 2 | No | Yes | 100 MU/ton | No | 11.230[a] | 8.841[a] | 1.402[c] | 1.424[d] | 0.678[a] | 0.548[a] | 0.720[a] | 0.00[c] | 0.00[c] | 1.416 |
| 3 | Yes | No | No | No | 10.497[bcd] | 8.155[bc] | 1.669[a] | 1.704[a] | 0.538[d] | 0.429[c] | 0.579[d] | 1.38[a] | 1.56[a] | 1.579 |
| 4 | Yes | No | 100 MU/ton | No | 10.787[abc] | 8.435[abc] | 1.501[cd] | 1.536[c] | 0.611[bc] | 0.490[b] | 0.652[bc] | 1.16[ab] | 1.44[ab] | 1.465 |
| 5 | Yes | No | No | 1X Rec 10 U/lb | 10.456[cd] | 8.22[abc] | 1.560[bc] | 1.591b[c] | 0.594[c] | 0.477[b] | 0.635[c] | 1.34[a] | 1.19[bc] | 1.512 |
| 6 | Yes | No | No | 3X Rec 30 U/lb | 10.266[d] | 7.982[c] | 1.572[b] | 1.621[ab] | 0.597[c] | 0.483[b] | 0.638[c] | 1.16[ab] | 1.13[cd] | 1.526 |
| 7 | Yes | No | 100 MU/ton | 1X Rec 10 U/lb | 10.533[abc] | 8.227[abc] | 1.514[bc] | 1.536[c] | 0.598[c] | 0.482[b] | 0.639[c] | 1.09[b] | 1.25[bc] | 1.469 |
| 8 | Yes | No | 100 MU/ton | 3X Rec 30 U/lb | 10.496[bcd] | 8.156[bc] | 1.516[bc] | 1.562[bc] | 0.601[c] | 0.478[b] | 0.643[c] | 1.25[ab] | 1.38[abc] | 1.474 |
| 9 | Yes | Yes | No | No | 11.060[abc] | 8.658[ab] | 1.423[c] | 1.447[d] | 0.650[a] | 0.522[a] | 0.692[a] | 1.03[b] | 0.88[d] | 1.416 |
| 10 | Yes | Yes | No | 3X Rec 30 U/lb | 10.666[abc] | 8.359[abc] | 1.430[e] | 1.444[d] | 0.647[ab] | 0.526[a] | 0.688[ab] | 1.03[b] | 1.13[cd] | 1.420 |

[1]I = Infection.
[2]M = Medication (Salinomycin (60 g/ton) and BMD (50 g/ton)).
[3]AF/G = weight adjusted feed conversion (Treatment 1 lbs$_{day\ 21}$-Treatment X lbs$_{day\ 21}$)/3) + (feed consumed/weight gain $_{(day\ 0-21)}$).
PI-PLC units are units based on Example 4.
Hemicell MU = million ChemGen units.

IV. Broiler Chicken Feeding Trial IV

The study was done in randomized Petersime battery cages to test the effect of PI-PLC, mannanase (U.S. Pat. No. 5,429,828) and fungal mannanase enzyme on male broiler performance reared to 21 days of age. Birds were challenged at 8 days of age with coccidia (75,000 E acervulina oocysts and 1,250 E. maxima oocysts per bird by oral gavage, and at 11, 12, and 13 days of age with Clostridium perfringens (oral gavage each day with fresh broth culture having 10[8] cfu/ml). Each of the treatments had 8 replications or cages. Each cage initially housed 14 Mareks-vaccinated, Cobb× Cobb male broilers (reduced to 10 on Day 14 as 4 birds were removed for lesion-scoring) with a spacing of 0.36 ft[2]/bird. Birds were not replaced. Feed and water was fed ad libitum throughout the entire trial test period (Days 0 to Day 21). Diets were fed in MASH from 0–21 days of age. The basal feed for treatments 1 through 16 was a typical corn/soy broiler starter feed containing 22% crude protein, with an ME of 1400 kcal/lb.

The results summarized in Table 10 below demonstrates the reproducible benefit of adding either PI-PLC or mannanase into the feeds of broiler chickens infected with two species of avian coccidian and Clostridium perfringenes causing improvement in both weight gain and feed conversion. Importantly, this study shows that either the PI-PLC or mannanase when combined with salinomycin, but without the antibiotic BMD (Tests 6 and 5) restores the performance to basically the level of the uninfected tests (No. 1 and 2). This provides evidence for antibacterial function. In this instance, the PI-PLC/Salinomycin performed somewhat better than the mannanase, and out performed even the current practice in the U.S. of adding BMD and salinomycin combination for infected flocks (Test 4).

TABLE 10

Broiler Chicken Feeding Trial IV

| | | | | Lesion Score | | | | | | Live |
|---|---|---|---|---|---|---|---|---|---|---|
| | | | | E. acer. | E. max. | Feed Conversion | | Weight Gain | | Weight |
| Test | I[1] | E[2] | M[3] | Upper | Middle | Day 0–21 | Day 8–21 | Day 0–21 | Day 8–21 | Day 21 |
| 1 | – | – | – | 0.00 | 0.00 | 1.652 | 1.694 | 0.527 | 0.427 | 0.565 |
| 2 | – | – | B/S | 0.00 | 0.00 | 1.612 | 1.656 | 0.546 | 0.437 | 0.583 |
| 3 | + | – | – | 2.44 | 2.31 | 1.813 | 1.909 | 0.394 | 0.296 | 0.432 |
| 10 | + | – | B | 2.25 | 1.94 | 1.707 | 1.770 | 0.453 | 0.352 | 0.490 |
| 7 | + | – | S | 1.00 | 1.09 | 1.709 | 1.719 | 0.458 | 0.368 | 0.496 |
| 4 | + | – | B/S | 0.59 | 1.63 | 1.585 | 1.671 | 0.509 | 0.397 | 0.547 |
| 16 | + | PI-PLC | – | 2.25 | 1.50 | 1.701 | 1.778 | 0.451 | 0.347 | 0.486 |
| 9 | + | PI-PLC | B | 2.03 | 1.34 | 1.760 | 1.844 | 0.445 | 0.342 | 0.482 |
| 6 | + | PI-PLC | S | 1.06 | 1.28 | 1.584 | 1.613 | 0.526 | 0.419 | 0.564 |
| 12 | + | Man. | – | 1.94 | 1.34 | 1.803 | 1.849 | 0.433 | 0.338 | 0.483 |
| 13 | + | Man. 5× | – | 2.13 | 2.00 | 1.740 | 1.813 | 0.437 | 0.339 | 0.471 |

TABLE 10-continued

Broiler Chicken Feeding Trial IV

| | | | Lesion Score | | Feed Conversion | | Weight Gain | | Live Weight |
|---|---|---|---|---|---|---|---|---|---|
| | | | E. acer. | E. max. | | | | | |
| Test | I[1] | E[2] | M[3] | Upper | Middle | Day 0–21 | Day 8–21 | Day 0–21 | Day 8–21 | Day 21 |
| 8 | + | Man. | B | 2.09 | 1.34 | 1.707 | 1.772 | 0.448 | 0.348 | 0.486 |
| 5 | + | Man. | S | 0.97 | 1.09 | 1.652 | 1.688 | 0.500 | 0.397 | 0.538 |
| 11 | + | Man. | B/S | 0.78 | 1.16 | 1.622 | 1.666 | 0.502 | 0.390 | 0.540 |

[1]I = Infection: challenged at 8 days of age with 75,000 E. acervulina oocysts and 1,250 E. maxima oocysts per bird by oral gavage, and at 11, 12, and 13 days of age with Clostridium perfringens by oral gavage with 1 mL fresh broth culture having $10^8$ cfu/ml.
[2]E = Enzymes: PI-PLC = recombinant PI-PLC produced by B. megaterium added at 30 U/lb, units defined as in Example 4; Man. = B. lentus endo-1,4- -D-mannanase (U.S. Pat. 5,429,828) added at 121 MU/ton (millions of ChemGen units/ton), or 5× at 506 MU/ton.
[3]M = Medication (B = BMD at 50 g/ton); 8 = Salinomycin(at 60 g/ton).

EXAMPLE 12

Determination of the Effect of Enzymes on Viability and Cellular Invasion by *Eimeria acervulina* and *Eimeria tenella* Sporozoites in vitro

*Eimeria acervulina* sporozoites or *Eimeria tenella* sporozoites and cultured baby hamster kidney (BHK) cells were prepared by published methods. See Augustine, *Avian and Poultry Biology Reviews* 11:113–122, 2000. For cell pretreatment, cell cultures were overlaid with dilutions of enzymes as described in Table 11, and examined for morphological changes from 5 to 45 min post overlay. After 45 minutes, the monolayer cultures were washed twice, then inoculated with untreated *E. acervulina* or *E. tenella* sporozoites. For application during infection, sporozoites were suspended in the appropriate dilution of the enzyme and inoculated immediately into the cell cultures. After 45 minutes incubation, cultures were fixed, stained, and the invasion was quantified.

Observations were made looking for changes in gross morphology of sporozoites or cells due to enzyme treatment. At the enzyme levels used in these experiments, no morphological change was noted. The sporozoite invasion of the cultured cells was measured after the two methods of enzyme treatment, as well as without enzyme treatment, by histological staining and microscopy procedures. See Augustine, supra.

The data in Table 11 show significant reductions in sporozoite invasion with both *E. acervulina* or *E. tenella* sporozoite invasions. Both the relatively impure PI-PLC enzyme preparation from *B. cereus* extracellular broth, and the highly pure recombinant PI-PLC produced in recombinant *B. megaterium* broth resulted in a statistically significant reduction of invasion in most experiments. Even at dose approximately one-half of the *B. cereus* wild type PI-PLC preparation, the recombinant PI-PLC preparation was still active. Thus, pretreatment of the cells with the enzyme and washing away of the enzyme was as effective as adding the enzyme concurrently during the infection. However, based on the experience with extracting enzyme from feed, the two wash steps likely do not remove all of the enzyme.

An enzyme preparation with endo-1,4-D-mannanase also caused statistically significant reduction of invasion in two experiments where the cells were pre-treated with enzyme before infection. These positive results included one experiment with each pathogen type. Therefore, mannanase also performed as well as the *B. cereus* PI-PLC preparation to reduce sporozoite invasion in vitro.

TABLE 11

In vitro invasion of BHK cells by *Eimeria acervulina* or *Eimeria tenella* sporozoites with and without enzyme treatments.

| | Cell Pretreatment with Enzyme Followed by Wash | | Application of Enzyme During Infection | |
|---|---|---|---|---|
| Enzymes and Concentrations | Test 1 | Test 2 | Test 1 | Test 2 |
| *E. acervulina* sporozoites | | | | |
| Control | 22 ± 1[a] | 33 ± 4[a] | 50 ± 4[a] | 35 ± 7[a] |
| PI-PLC from *B. cereus*[1] 0.0403 U/mL | 15 ± 1[b] | 26 ± 1[ab] | 33 ± 3[b] | 25 ± 2[ab] |
| PI-PLC from Recombinant *B. megateriaum*[2] 0.261 U/mL | 14 ± 1[b] | 22 ± 1[b] | 16 ± 2[c] | 18 ± 1[bc] |
| PI-PLC from Recombinant *B.* megateriaum 0.0261 U/mL | 18 ± 1[b] | 26 ± 1[ab] | 36 ± 3[b] | 9 ± 2[c] |
| endo-1,4- -D-mannanase[3] 5100 U/mL | 16 ± 1[b] | 29 ± 2[ab] | ND[4] | ND |
| *E. tenella* sporozoites | | | | |
| Control | 44 ± 2[a] | 26 ± 4[a] | 63 ± 5[a] | 42 ± 4[a] |
| PI-PLC from *B. cereus*[1] 0.0403 U/mL | 38 ± 2[b] | 21 ± 2[a] | 52 ± 13[ab] | 37 ± 2[ab] |
| PI-PLC from Recombinant *B. megateriaum*[2] 0.261 U/mL | 30 ± 1[c] | 15 ± 0[a] | 28 ± 2[b] | 39 ± 4[ab] |
| PI-PLC from Recombinant *B. megateriaum*[2] 0.0261 U/mL | ND | 17 ± 1[a] | 18 ± 1[c] | 29 ± 1[b] |
| endo-1,4- -D-mannanase[3] 5100 U/mL | 35 ± 1[b] | 19 ± 5[a] | 46 ± 6[ab] | ND |

Invasion counts are reported as mean ± standard error of the mean measured from 1–3 coverslips/abenation (BHK cells were grown on coverslips inserted in culture dishes). Means within test groups with different superscripts differ significantly (P < or = 0.05).
[1]Extracellular enzyme from *B. cereus* dialyzed in phosphate-buffered saline, units standardized to the method of Example 4.
[2]Extracellular enzyme from recombinant *B. megaterium* dialyzed in phosphate-buffered saline, units standardized to the method of Example 4.
[3]Mannanase obtained from *Bacillus lentus* as described in U.S. Pat. 5,429,828 and dialyzed into phosphate-buffered saline, units are as defined by the ChemGen Corp. reducing sugar assay.
[4]ND = not determined.

EXAMPLE 13

In vitro Evaluation of PI-PLC for Cryptosporidium Infection

The enzyme PI-PLC was evaluated for anti-cryptosporidial activity and toxicity at concentrations ranging from 0.001–30 U/ml were performed using 4-day-old Madin-Darby canine kidney (MDCK) cells. Enzyme units were defined as by the method in Example 4 but measured as in Example 9. The preparation of enzyme used was from recombinant *Bacillus megaterium*. Treatment was initiated 3 hours after infection and continued through 48 hours.

Chemiluminescence Immunoassay

Before infection, oocysts were washed and resuspended in DMEM base with 0.75% sodium taurocholate and incubated for 10 min at 37° C. (You et al., *FEMS Microbiol. Letters* 136:251–256, 1996; You et al., *J. Antimicrobial. Chemother.* 41:293–296, 1998). The excystation mixture was diluted with Ultraculture medium, promptly dispensed in plates containing MDCK cells, at 100% confluence, and maintained in Ultraculture medium for 4 days. The inoculum was incubated with the cells for 3 h before washing with PBS and replaced with fresh Ultraculture medium with or without test enzyme. Plates were incubated at 37° C., in a 5% $CO_2$ air atmosphere for 48 h. Cultures were washed with PBS and fixed with Bouin's solution.

The fixed plates were washed with TBST buffer (20 mM Tris-HCl (pH 7.5), 150 mM NaCl, 0.05% Tween-20) and blocked with 1% BSA-TBST (TBST buffer containing 1% bovine serum albumin) for 30 min at 25° C. with gentle shaking. Rabbit anti-*Cryptosporidium parvum* sera (1:200 dilution) was applied to the plates and incubated for 1 hr. After washing with TBST, the samples were sequentially incubated with biotin-labeled goat anti-rabbit 1 gG and horseradish peroxidase-labeled streptavidin (working dilution, 1:1000, KPL Inc., Gaithersburg, Md.). Enhanced Luminol (4-iodophenol and hydrogen peroxide, Aldrich Chemical Co. Inc., Milwaukee, Wis.) was used as a substrate. The plates were read with an ML3000 Luminometer (Dynatech Lab., Chantilly, Va.) and the relative light units (RLU) were determined. Means of RLU were calculated from 4 replicate wells and all experiments were repeated at least twice.

Toxicity Assay.

The enzyme was tested using a commercial tetrazolium dye reduction assay (CellTiter 96; Promega Corp., Madison, Wis., USA). Briefly, each enzyme concentration indicated below was introduced into 96-well plates containing confluent MDCK cell monolayers. Each dilution was evaluated in triplicate. Enzyme was incubated on the monolayers at 37° C. and 5% $CO_2$. At 48 hours, plates were developed for 1 hr and read in the ELISA plate reader at 490 nm. Results were recorded and analyzed. Percent toxicity was calculated by subtracting the mean OD of the medium control without the enzyme from the mean OD with the enzyme and then divided by the OD of the medium and multiplied by 100. Cytotoxicity scores were assigned as indicated in the following table.

| Toxicity % | Score |
| --- | --- |
| 0–5% | 0 |
| 6–25% | 1 |
| 26–50% | 2 |
| 51–75% | 3 |
| 76–100% | 4 |

Significant toxicity was observed with 3 U/mL or with higher concentration of the enzyme. No significant toxicity was observed with this enzyme in the range of 0.1–1 U/mL (Table 12). Therefore, a set of experiments in this concentration range (1.0 U/mL or lower) was performed to determine activity of the enzyme and specificity of the enzyme. In the first experiment, MDCK cells were infected with excysted sporozoites. After a 3-hour incubation period, the cell monolayer was washed and the enzyme was added at various concentrations for a 48-hour period. As shown in Table 13, the enzyme demonstrated anti-cryptosporidial activity in the range of 0.01–1 U/mL in vitro. Approximately 50% inhibition was achieved at a concentration of 0.1 U/mL (FIG. 1).

TABLE 12

Toxicity of recombinant PI-PLC prepared in
*B. megaterium* to MDCK monolayer cell cultures

| Concentration | % Toxicity (95% CL) | Toxicity Score |
| --- | --- | --- |
| 10 U/mL | 83 | 4 |
| 3 | 57 | 3 |
| 1 | 13 | 1 |
| 0.3 | 11 | 1 |
| 0.1 | 10 | 1 |

TABLE 13

Activity of the recombinant PI-PLC enzyme with
*C. parvum* infected MDCK cell cultures

| Treatment | Unit/mL | Percent Inhibition | Mean Number of Cryptosporidium per microtiter plate well | 95% CL |
| --- | --- | --- | --- | --- |
| Post Infect for 3 h | 1 | 77.36 | 285.28 | 0.01 |
|  | 0.3 | 77.26 | 286.5 | 0.04 |
|  | 0.1 | 52.74 | 595.53 | 0.18 |
|  | 0.03 | 27.62 | 912.15 | 0.22 |
|  | 0.01 | 7.33 | 1167.78 | 0.09 |
| Infected | — | 0 | 1260.18 | 0.09 |
| Uninfected | — | 100 | 0 | 0.02 |

A second set of experiments were performed to evaluate enzyme specificity. Sporozoites were treated with the enzyme at various concentrations for 45 min and briefly washed. The treated sporozoites were then allowed to infect untreated host cells and develop and reproduce for 48 hours. In a separate experiment, host cells were incubated with the enzyme at various concentrations, washed and infected with untreated sporozoites. As shown below (Table 14), treatment of either sporozoite or host cells with the enzyme results in partial inhibition. A dose dependent inhibition was not observed in this concentration range. This may be due to the short incubation period of the enzyme with host or parasite cells (45 min) or partial or incomplete cleavage of host/parasite receptors. Additionally, other host/parasite receptors are probably involved in infection and account for the growth observed in the host cells.

TABLE 14

Pre-Infection treatment of sporozoites or MDCK cells
and the effect on infectivity of *C. parvum*.

| Treatment | PI-PLC Unit/ml | Percent Inhibition | Mean Number of Cryptosporidium per microtiter plate well | 95% CL |
| --- | --- | --- | --- | --- |
| Sporozoite treated before infection | 1 | 67.27 | 412.40 | 0.02 |
|  | 0.3 | 65.64 | 433.04 | 0.06 |
|  | 0.1 | 57.40 | 536.80 | 0.03 |
|  | 0.03 | 58.13 | 527.59 | 0.03 |
|  | 0.01 | 56.98 | 542.15 | 0.01 |
| Host cells treated before infection | 1 | 68.76 | 393.64 | 0.12 |
|  | 0.3 | 50.07 | 629.24 | 0.26 |
|  | 0.1 | 63.82 | 455.88 | 0.19 |
|  | 0.03 | 58.53 | 522.66 | 0.12 |
|  | 0.01 | 56.84 | 543.85 | 0.10 |

TABLE 14-continued

Pre-Infection treatment of sporozoites or MDCK cells and the effect on infectivity of C. parvum.

| Treatment | PI-PLC Unit/ml | Percent Inhibition | Mean Number of Cryptosporidium per microtiter plate well | 95% CL |
|---|---|---|---|---|
| Infected | 0 | 0 | 1260.18 | 0.09 |
| Uninfected | 100 | 100 | 0 | 0.02 |

EXAMPLE 14

In vivo Evaluation of PI-PLC for Cryptosporidium Infection

The enzyme was evaluated for anticryptosporidial efficacy using an immunodeficient SCID mouse model. Briefly, oocyst inocula were prepared by washing purified oocysts (stored <6 months) with 0.1% BSA, PBS (pH 7.2) to remove potassium dichromate. SCID mice (4–5 week old) were infected with $10^6$ oocysts (IOWA strain) and treated as indicated below. Fecal samples were collected from the mice, purified through discontinuous sucrose and assessed for parasite load by flow cytometry as previously described. See Arrowwood et al., *J. Parasitol.* 81:404–409, 1995.

TABLE 15

Treatment Regimen For Therapeutic Experiments

| Mouse Group | A | B | C |
|---|---|---|---|
| Number of mice | 10 | 10 | 10 |
| Inoculum Dose | $10^6$ | $10^6$ | $10^6$ |
| Compound | PI-PLC | PI-PLC | Placebo |
| Dose (mg/Kg) | 90 U/ml | 30 U/ml | PBS |
| Route | Given in feed | Given in feed | Given in feed |
| Frequency | Ad lib | Ad lib | Ad lib |

Granulated mouse chow was coated with either 30 or 90 U/lb of PI-PLC in PBS or PBS. All mice were fed by ad libitum. Mice received feed immediately after infection. Fecal samples and weights were collected twice per week. Consumption of feed was measured daily. Mice were euthanized by injecting each with 0.2 cc of 100 mg/ml Ketamine, 100 mg/ml Xylazine, and 0.9% NaCl).

Average feed consumed per day per mouse and average mouse weights are shown in Table 16. No statistically significant difference in consumption of feed or weight were observed over the 3 week period.

TABLE 16

Feed consumption and weight gain of mice.

| | Treatment Groups | Feed (g) consumed/mouse/day | Weight (g) |
|---|---|---|---|
| Day 3 | | AVG | AVG |
| | A (90 U/lb) | 7.56 | 16.67 |
| | B (30 U/lb) | 6.13 | 17.055 |
| | C (PBS control) | 5.46 | 16.88 |
| Day 7 | | AVG | AVG |
| | A | 8.31 | 16.95 |
| | B | 8.51 | 16.91 |
| | C | 7.27 | 16.89 |
| Day 10 | | AVG | AVG |
| | A | 8.55 | 17.29 |
| | B | 7.93 | 17.08 |
| | C | 7.11 | 16.97 |
| Day 14 | | AVG | AVG |
| | A | 7.78 | 17.43 |
| | B | 8.06 | 17.62 |
| | C | 7.55 | 17.38 |
| Day 17 | | AVG | AVG |
| | A | 8.52 | 17.64 |
| | B | 8.53 | 17.84 |
| | C | 7.79 | 17.59 |
| Day 21 | | AVG | AVG |
| | A | 7.89 | 18.25 |
| | B | 8.22 | 18.62 |
| | C | 8.51 | 18.14 |
| Day 24 | | AVG | AVG |
| | A | 9.79 | 18.2 |
| | B | 8.3 | 18.63 |
| | C | 8.22 | 18.33 |

Efficacy at 3 Weeks Post Infection

Feces samples were collected at 3, 4 and 4.5 weeks post-infection and the Cryptosporidium counts in 100 microliter samples were measured from SCID mice in treated and control groups as shown in Table 17. As shown, mice treated with the enzyme demonstrated a reduction in parasite load. Parasite loads were observed (34–54%) in the treated groups. Some of these reductions were statistically significant when evaluated using ANOVA statistical analysis (shown below and marked with a symbol). The enzyme demonstrates potential as an anti-cryptosporidial therapeutic agent. Higher doses of the enzyme or better delivery of the enzyme to the infection site could increase its efficacy and may be addressed in future experiments.

TABLE 17

Efficacy of PI-PLC in vivo to reduce Cryptosporidium in feces

| Treatment Group | Enzyme Dose (U/lb) | Parasite load (oocysts/100 µl) (SD) Day 21 | Percent Inhibition | Parasite load (oocysts/100 µl) (SD) Day 28 | Percent Inhibition | Parasite load (oocysts/100 µl) (SD) Day 31 | Percent Inhibition |
|---|---|---|---|---|---|---|---|
| PI-PLC | 90 | 22.7 (11.4) | 44.0 | 26.3 (14)* | 48.9 | 87.5 (52.9) | 34.0 |
| PI-PLC | 30 | 16.2 (4.7) | 52.0 | 23.4 (11)* | 54.6 | 74.3 (89.7)⁺ | 40.0 |
| PBS (control) | — | 33.5 (16.2) | — | 50.4 (29) | — | 132.1 (89.) | — |

*P values were significant at 0.05 or less.
+P value was 0.08 or less.

EXAMPLE 15
Verification of Enzyme in Feeds Used Growth Tests

Assay of PI-PLC extracted from feeds used in the above animal trials was conducted as described in Example 10. The results are summarized in Tables 18–19.

TABLE 18

Cryptosporidium Study, Mouse Feed

| Treatment | Control | 30 U/lb | 90 U/lb |
|---|---|---|---|
| Target U/lb | 0 | 30 | 90 |
| PI-PLC Type | — | Recombinant from B. megaterium | Recombinant from B. megaterium |
| PI-PLC Lot No. | — | 45–46 SF | 45–46 SF |
| Assays U/lb Extracted | 0 | 22.8 | 66.1 |
| % of Target Extracted | — | 76.0 | 73.4 |

The efficiency of the extraction from feed varied significantly with type of feed. The extraction out of mouse feed showed 73.4 to 76 percent efficiency (Table 18). Three different preparations of chicken feed made at three different sites were carefully loaded with 45 or 180 U/lb of recombinant PI-PLC, then immediately extracted and assayed using the assay procedure of Example 9 as the loading level is in range of the continuous assay method of Example 9 (Table 19).

TABLE 19

Testing of Extraction Efficiency from Different Chicken Feed Sources and Corn Meal

| | Source of Chicken Feed | | | | | | Corn Meal | |
|---|---|---|---|---|---|---|---|---|
| | Source 1 | | Source 2 | | Source 3 | | | |
| Loading Level Units/Lb | 180 | 45 | 180 | 45 | 180 | 45 | 180 | 45 |
| Units/lb Extracted | 128 | 9.3 | 53.2 | 3.66 | 82.7 | 8.46 | 134.4 | 33 |
| % of Added Units Extracted | 71.1 | 20.7 | 29.6 | 8.1 | 45.9 | 18.8 | 74.7 | 73.3 |

It can be seen that extraction efficiency from corn meal is similar to extraction from mouse feed. However, extraction from some chicken feed samples was poor in this experiment, and also in others.

In the test as shown in Table 20, the extractable enzyme was approximately 30–45% of the theoretical PI-PLC whereas the β-mannanase was readily extractable and the yield was approximately 100%. About 45% extraction was the best level of extraction seen with this feed with the extraction test shown above. Thus, the assay results for U/lb. extracted for the feeds of the test of Table 20 are in the range expected for the loading used.

TABLE 20

Verification of Enzyme Loading on Broiler Chicken Trial III

| Treatment No. | 1 | 2 | 3 | 4 | 5 | 6 | 7 | 8 | 9 | 10 |
|---|---|---|---|---|---|---|---|---|---|---|
| Infection | − | − | + | + | + | + | + | + | + | + |
| Medication | + | + | − | − | − | − | − | − | + | + |
| Target Unit/lb | 0 | 0 | 0 | 0 | 10 | 30 | 10 | 30 | 0 | 30 |
| PI-PLC Type | − | − | − | − | WT | Rec | Rec | Rec | − | Rec |
| *Assays Unit/lb of PI-PLC* | | | | | | | | | | |
| Average Unit/lb | 0.94 | 0.76 | 0.79 | 0.7 | 3.08 | 11.48 | 4.56 | 10.18 | | 9.49 |
| Percent Target | − | − | − | − | 30.75 | 38.27 | 45.57 | 33.93 | | 31.64 |
| Target MU/ton | − | 100 | − | 100 | − | − | 100 | 100 | − | − |
| Hemicell Mannanase | − | + | − | + | − | − | + | + | − | − |
| *Assays MU/ton of Mannanase* | | | | | | | | | | |
| MU/ton | − | 124.9 | − | 135.5 | − | − | 153.5 | 172.0 | − | − |
| Percent Target | − | 124.9 | − | 135.5 | − | − | 153.5 | 172.0 | − | − |

While certain representative embodiments and details have been shown for the purpose of illustrating the invention, it will be apparent to those skilled in the art that various changes and modifications may be made therein without departing from the scope of the invention.

What we claim is:

1. A composition comprising (i) an enzyme that effects cleavage of a linkage that is comprised of a phosphatidylinositol and that membrane-anchors a surface protein or a carbohydrate on a pathogen, whereby said cleavage effects release of said surface protein or carbohydrate and (ii) a physiologically acceptable carrier for said enzyme, wherein said composition is in a form suitable for oral administration to a host and wherein said cleavage interferes with pathogen binding to a host cell in the intestines, such that the infective ability of said pathogen to said host cell is reduced.

2. The composition according to claim 1, wherein said composition is a feed.

3. The composition according to claim 1, wherein said composition contains no anti-infection agent other than said enzyme.

4. The composition according to claim 1, wherein said enzyme cleaves a linkage that effects release of a cell-surface protein.

5. The composition according to claim 1, wherein said enzyme is a type C or type D phospholipase.

6. The composition according to claim 5, wherein said type C phospholipase is a phosphatidylinositol-specific phospholipase C.

7. The composition according to claim 1, wherein said composition further comprises a stabilizer, a carbohydrate carrier or a preservative.

8. The composition according to claim 7, wherein said stabilizer is a buffer, a carbohydrate or a glycol.

9. The composition according to claim 7, wherein said carbohydrate carrier is selected from the group consisting of xylose, fructose, glucose, sorbitol, and maltotriose.

10. The composition according to claim 7, wherein said preservative is selected from the group consisting of propylparaben, sodium sorbate, potassium sorbate, and ascorbyl palmitate.

11. The composition according to claim 1, wherein said carrier is a foodstuff into which said enzyme is incorporated.

12. The composition according to claim 11, wherein said foodstuff is an animal feed comprised of grain material, a source of protein, vitamins, amino acids, and minerals.

13. The composition according to claim 12, wherein said grain material is corn, sorghum, wheat, barley or oats.

14. The composition according to claim 12, wherein said source of protein is beans or peas.

15. The composition according to claim 1, wherein said composition is in a solid or a liquid formulation.

16. The composition according to claim 1, wherein said enzyme is contained in a tablet or a gelatin capsule shell.

17. The composition according to claim 1, wherein said enzyme is prepared from a *Bacillus cereus* strain.

18. The composition according to claim 17, wherein said *Bacillus cereus* strain is ATCC 7004 or ATCC 6464.

19. The composition according to claim 1, wherein said enzyme is obtained by expression of a recombinant DNA in a host organism.

20. The composition according to claim 19, wherein said host organism is from a *Bacillus megaterium* strain.

21. The composition according to claim 2, wherein said enzyme is present at 200 IU/Kg–4000 IU/Kg feed.

22. The composition according to claim 5, wherein said phospholipase is 1-phosphatidylinositol phosphodiesterase.

23. The composition according to claim 5, wherein said type C phospholipase belongs to enzyme class, E.C. 3.1.4.10.

24. The composition according to claim 5, wherein said phospholipase is glycosyl-phosphatidylinositol-specific phospholipase D.

25. A method of treating or ameliorating the risk of a digestive tract infection, comprising orally administering, to a subject suffering from or at risk for suffering said infection, an effective amount of said composition according to claim 1.

26. The method according to claim 25, wherein said enzyme cleaves a linkage that effects release of a cell-surface protein.

27. The method according to claim 25, wherein said method does not include administering an anti-infection agent other than said enzyme.

28. The method according to claim 25, wherein said infection is caused by a protozoan, bacterial, yeast, or fungal pathogen.

29. The method according to claim 28, wherein said infection is caused by a protozoan pathogen of the genus Eimeria.

30. The method according to claim 28, wherein said infection is caused by a protozoan pathogen of the genus Cryptosporidium.

31. The method according to claim 28, wherein said infection is caused by a bacterial pathogen of the genus Clostridium.

32. The method according to claim 25, comprising administering orally, to said subject, an extracellular enzyme preparation from a *Bacillus cereus* strain.

33. The method according to claim 32, wherein said *Bacillus cereus* strain is ATCC 7004 or ATCC 6464.

34. The method according to claim 25, wherein said enzyme is obtained by expression of a recombinant DNA in a host organism.

35. The method according to claim 34, wherein said host organism is from a *Bacillus megaterium* strain.

36. The composition according to claim 2, wherein said enzyme is present at 3 U/lb feed.

37. The composition according to claim 2, wherein said enzyme is present at 10 U/lb feed.

38. The composition according to claim 2, wherein said enzyme is present at 30 U/lb feed.

39. The composition according to claim 2, wherein said enzyme is present at 90 U/lb feed.

* * * * *

UNITED STATES PATENT AND TRADEMARK OFFICE
CERTIFICATE OF CORRECTION

PATENT NO. : 6,780,628 B2
DATED : August 24, 2004
INVENTOR(S) : Anderson et al.

It is certified that error appears in the above-identified patent and that said Letters Patent is hereby corrected as shown below:

Title page,
Item [*] Notice, should read:
-- Subject to any disclaimer, the term of this patent is extended or adjusted under 35 U.S.C.154(b) by 170 days --

Signed and Sealed this

Seventeenth Day of May, 2005

JON W. DUDAS
*Director of the United States Patent and Trademark Office*